United States Patent
Dantas et al.

(10) Patent No.: US 10,500,191 B2
(45) Date of Patent: Dec. 10, 2019

(54) COMPOSITIONS AND METHODS OF USE OF ANTIBACTERIAL DRUG COMBINATIONS

(71) Applicant: Washington University, St. Louis, MO (US)

(72) Inventors: Gautam Dantas, St. Louis, MO (US);
Patrick Gonzales, St. Louis, MO (US);
Kevin Forsberg, St. Louis, MO (US);
Mitchell Pesesky, St. Louis, MO (US);
Mayland Chang, St. Louis, MO (US);
Shahriar Mobashery, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 0 days.

(21) Appl. No.: 15/743,203

(22) PCT Filed: Jul. 8, 2016

(86) PCT No.: PCT/US2016/041565
§ 371 (c)(1),
(2) Date: Jan. 9, 2018

(87) PCT Pub. No.: WO2017/008034
PCT Pub. Date: Jan. 12, 2017

(65) Prior Publication Data
US 2018/0200226 A1 Jul. 19, 2018

Related U.S. Application Data

(60) Provisional application No. 62/190,588, filed on Jul. 9, 2015.

(51) Int. Cl.
| | |
|---|---|
| A61K 31/43 | (2006.01) |
| A61K 31/407 | (2006.01) |
| A61K 31/546 | (2006.01) |
| A61K 45/06 | (2006.01) |
| A61K 31/424 | (2006.01) |
| A61K 31/431 | (2006.01) |
| A61P 31/04 | (2006.01) |
| A61K 31/496 | (2006.01) |

(52) U.S. Cl.
CPC .......... *A61K 31/407* (2013.01); *A61K 31/424* (2013.01); *A61K 31/43* (2013.01); *A61K 31/431* (2013.01); *A61K 31/496* (2013.01); *A61K 31/546* (2013.01); *A61K 45/06* (2013.01); *A61P 31/04* (2018.01)

(58) Field of Classification Search
CPC ...... A61K 31/43; A61K 2300/00; A61P 31/04
See application file for complete search history.

(56) References Cited

U.S. PATENT DOCUMENTS

2010/0173887 A1 7/2010 Pfaendler et al.

FOREIGN PATENT DOCUMENTS

| WO | 2010025328 A1 | 3/2010 |
|---|---|---|
| WO | 2013014497 A1 | 1/2013 |
| WO | 2013085152 A1 | 6/2013 |
| WO | 2014033561 A1 | 3/2014 |
| WO | 2014170683 A1 | 10/2014 |
| WO | 2016176634 A1 | 11/2016 |
| WO | 2017008034 A1 | 1/2017 |
| WO | 2017203266 A1 | 11/2017 |

OTHER PUBLICATIONS

Neu HC, Fu KP. Synergistic activity of piperacillin in combination with beta-lactamase inhibitors. Antimicrob Agents Chemother. Oct. 1980;18(4):582-5. PubMed PMID: 6255862; PubMed Central PMCID: PMC284053. (Year: 1980).*
Perry CM, Markham A. Piperacillin/tazobactam: an updated review of its use in the treatment of bacterial infections. Drugs. May 1999;57(5):805-43. Review. PubMed PMID: 10353303. (Year: 1999).*
Zhanel GG, Wiebe R, Dilay L, Thomson K, Rubinstein E, Hoban DJ, Noreddin AM, Karlowsky JA. Comparative review of the carbapenems. Drugs. 2007;67(7):1027-52. Review. PubMed PMID: 17488146. (Year: 2007).*
Otero, L. et al., "How allosteric control of *Staphylococcus aureus* penicillin binding protein 2a enables methicillin resistance and physiological function," PNAS, Oct. 15, 2013, pp. 16808-16813, vol. 110, No. 42, with Supporting Information, pp. 1-10.
Petinaki, E. et al., "Detection of mecA, mecR1 and mecI genes among clinical isolates of methicillin-resistant staphylococci by combined polymerase chain reactions," J. Antimicrob. Chemother., 2001, pp. 297-304, vol. 47.
"PRIMAXIN (imipenem and cilastatin) for injection, for intravenous use," Merck & Co., Inc., Oct. 2014, pp. 1-17.
Rice, L. "Antimicrobial Resistance in Gram-Positive Bacteria," Am. J. Med., Jun. 2006, pp. S11-S19, vol. 119, No. 6A, Elsevier Inc.
Saiman, L., "Clinical utility of synergy testing for multidrug-resistant Pseudomonas aeruginosa isolated from patients with cystic fibrosis: 'the motion for'," Paediatric Respiratory Rev., 2007, pp. 249-255, vol. 8, Elsevier Ltd.
Sjolund, M. et al., "Long-Term Persistence of Resistant *Enterococcus* Species after Antibiotics to Eradicate Helicobacter pylori," Ann. Intern. Med., Sep. 16, 2003, pp. 483-487, vol. 139, No. 6.
Somani, P. et al., "Pharmacokinetics of Imipenem-Cilastatin in Patients with Renal Insufficiency Undergoing Continuous Ambulatory Peritoneal Dialysis," Antimicrobial Agents and Chemotherapy, Apr. 1988, pp. 530-534, vol. 32, No. 4.
Sonstein, S. et al., "Loss of the Penicillinase Plasmid After Treatment of *Staphylococcus aureus* with Sodium Dodecyl Sulfate," J. Bacteriol., Jan. 1972, pp. 262-265, vol. 109, No. 1.
Spratt, B., "Properties of the Penicillin-Binding Proteins of *Escherichia coli* K12," Eur. J. Biochem., 1977, pp. 341-352, vol. 72.

(Continued)

*Primary Examiner* — Theodore R. West
(74) *Attorney, Agent, or Firm* — Polsinelli PC

(57) ABSTRACT

The present disclosure encompasses antibacterial compositions and methods of treating bacterial infections caused by resistant bacteria.

8 Claims, 14 Drawing Sheets
Specification includes a Sequence Listing.

(56) References Cited

OTHER PUBLICATIONS

Stutman, H. et al., "In Vitro Antimicrobial Activity of Aztreonam Alone and in Combination Against Bacterial Isolates from Pediatric Patients," Antimicrobial Agents and Chemotherapy, Feb. 1984, pp. 212-215, vol. 25, No. 2.
"SYBR® Select Master Mix for CFX User Guide," Applied Biosystems by Life Technologies, Apr. 2012, pp. 1-33.
Tupin, A. et al., "Resistance to rifampicin: at the crossroads between ecological, genomic and medical concerns," Accepted Manuscript, 2008, pp. 1-28, published as: International J. Antimicrob. Agents, 2010, pp. 519-523, vol. 35, No. 6.
Van Hal, S. et al., "Emergence of daptomycin resistance following vancomycin-unresponsive *Staphylococcus aureus* bacteraemia in a daptomycin-naive patient—a review of the literature," Eur. J. Clin. Microbiol. Infect. Dis., May 2011, pp. 603-610, vol. 30, No. 5, Springer.
Villegas-Estrada, A. et al., "Co-opting the Cell Wall in Fighting Methicillin-Resistant *Staphylococcus aureus*: Potent Inhibition of PBP 2a by Two Anti-MRSA beta-Lactam Antibiotics," NIH Public Access, Author Manuscript, available in PMC Sep. 21, 2009, pp. 1-5, published in final edited form as: J. Am. Chem. Soc., Jul. 23, 2008, pp. 9212-9213, vol. 130, No. 29.
Walsh, T. et al., "Dissemination of NDM-1 positive bacteria in the New Delhi environment and its implications for human health: an environmental point prevalence study," Lancet Infect. Dis., May 2011, pp. 355-362, vol. 11.
Waxman, D. et al., "Penicillin-Binding Proteins and the Mechanism of Action of Beta-Lactam Antibiotics," Ann. Rev. Biochem., 1983, pp. 825-869, vol. 52.
Wikler, M. et al., "Methods for Dilution Antimicrobial Susceptibility Tests for Bacteria That Grow Aerobically; Approved Standard—Eighth Edition," Clinical and Laboratory Standards Institute, Jan. 2009, pp. 1-65, vol. 29, No. 2, M07-A8.
Yang, et al., "Biochemical comparison of imipenem, meropenem and biapenem: permeability, binding to penicillin-binding proteins, and stability to hydrolysis by beta-lactamases," J. Antimicrob. Chemother., 1995, pp. 75-84, vol. 35.
Zhong, M. et al., "An interesting case of rifampicin-dependent/-enhanced multidrug-resistant tuberculosis," Int. J. Tuberc. Lung Dis., 2010, pp. 40-44, vol. 14, No. 1.
Zimmerman, G. et al., "Multi-target therapeutics: when the whole is greater than the sum of the parts," Drug Discovery Today, Jan. 2007, pp. 34-42, vol. 12, Nos. 1/2, Elsevier Ltd.
"ZOSYN (Piperacillin and Tazobactam) for Injection, USP," Pfizer Injectables, May 2012, 26 pgs.
Alekshun, M. et al., "Molecular Mechanisms of Antibacterial Multidrug Resistance," Cell, Mar. 23, 2007, pp. 1037-1050, vol. 128, Elsevier Inc.
Ankomah, P. et al., "The Pharmaco—, Population and Evolutionary Dynamics of Multi-drug Therapy: Experiments with *S. aureus* and *E. coli* and Computer Simulations," PLOS Pathogens, Apr. 2013, pp. 1-14, vol. 9, No. 4, e1003300.
Arede, P. et al., "Redefining the Role of the beta-Lactamase Locus in Methicillin-Resistant *Staphylococcus aureus*: beta-Lactamase Regulators Disrupt the MecI-Mediated Strong Repression on mecA and Optimize the Phenotypic Expression of Resistance in Strains with Constitutive mecA Expression," Antimicrobial Agents and Chemotherapy, Jul. 2013, pp. 3037-3045, vol. 57, No. 7.
Arias, C. et al., "Antibiotic-Resistant Bugs in the 21st century—A Clinical Super-Challenge," N. Engl. J. Med., Jan. 29, 2009, pp. 439-443, vol. 360, No. 5.
Barry, A. et al., "Methods for Determining Bactericidal Activity of Antimicrobial Agents; Approved Guideline," Clinical and Laboratory Standards Institute, Sep. 1999, pp. 1-29, vol. 19, No. 18, M26-A.
Berenbaum, M., "A Method for Testing for Synergy with any Number of Agents," J. Infectious Diseases, Feb. 1978, pp. 122-130, vol. 137, No. 2.
Berenbaum, M., "What is Synergy?," Pharmacol. Rev., Jun. 1989, pp. 93-141, vol. 41, No. 2.
Bhusal, Y. et al., "Determination of in vitro synergy when three antimicrobial agents are combined against Mycobacterium tuberculosis," International Journal of Antimicrobial Agents, Oct. 2005, pp. 292-297, vol. 26, No. 4, Elsevier.
Blazquez, B. et al., "Regulation of the Expression of the beta-Lactam Antibiotic-Resistance Determinants in Methicillin-Resistant *Staphylococcus aureus* (MRSA)," Biochem., 2013, pp. 1548-1550, vol. 53.
Boucher, H. et al., "Bad Bugs, No Drugs: No ESKAPE! An Update from the Infectious Diseases Society of America," Clinical Infectious Diseases, Jan. 1, 2009, pp. 1-12, vol. 48.
Cai, Y. et al., "Antibacterial Activity of Allicin Alone and in Combination with Beta-Lactams against *Staphylococcus* spp. and Pseudomonas aeruginosa," J. Antibiot., May 2007, pp. 335-338, vol. 60, No. 5.
Campbell, E. et al., "A Population Model Evaluating the Consequences of the Evolution of Double-Resistance and Tradeoffs on the Benefits of Two-Drug Antibiotic Treatments," PloS One, Jan. 2014, pp. 1-8, vol. 9, No. 1, e86971.
Chambers, H. et al., "Waves of Resistance: *Staphylococcus aureus* in the Antibiotic Era," NIH Public Access, Author Manuscript, available in PMC May 16, 2010, pp. 1-31, published in final form as: Nat. Rev. Microbiol., Sep. 2009, pp. 629-641, vol. 7, No. 9.
Cockerill, F. et al., "Performance Standards for Antimicrobial Susceptibility Testing; Nineteenth Informational Supplement," Clinical and Laboratory Standards Institute, Jan. 2009, pp. 1-149, vol. 29, No. 3, M100-S19.
Comas, I. et al., "Whole-genome sequencing of rifampicin-resistant M. tuberculosis strains identifies compensatory mutations in RNA polymerase," NIH Public Access, Author Manuscript, available in PMC Jul. 1, 2012, pp. 1-12, published in final edited form as: Nat. Genet., 2011, pp. 106-110, vol. 44, No. 1.
Craig, W., "The Pharmacology of Meropenem, A New Carbapenem Antibiotic," Clinical Infectious Diseases, 1997, pp. S266-S275, vol. 24, Suppl. 2.
Davies, J. et al., "Origins and Evolution of Antibiotic Resistance," Microbiol. Mol. Biol. Rev., Sep. 2010, pp. 417-433, vol. 74, No. 3.
Davies, J., "Microbes have the last word," EMBO Reports, 2007, pp. 616-621, vol. 8, No. 7.
Deryke, C. et al., "Bactericidal Activities of Meropenem and Ertapenem against Extended-Spectrum-beta-Lactamase-Producing *Escherichia coli* and Klebsiella pneumoniae in a Neutropenic Mouse Thigh Model," Antimicrobial Agents and Chemotherapy, Apr. 2007, pp. 1481-1486, vol. 51, No. 4.
Fischbach, M. et al., "Antibiotics for Emerging Pathogens," Sci., Aug. 28, 2009, pp. 1089-1093, vol. 325.
Fishovitz, J. et al., "Disruption of Allosteric Response as an Unprecedented Mechanism of Resistance to Antibiotics," J. Am. Chem. Soc., 2014, pp. 9814-9817, vol. 136.
Fuda, C. et al., "Activation for Catalysis of Penicillin-Binding Protein 2a from Methicillin-Resistant *Staphylococcus aureus* by Bacterial Cell Wall," J. Am. Chem. Soc., 2005, pp. 2056-2057, vol. 127.
Fuda, C. et al., "Beta-lactam resistance in *Staphylococcus aureus*: the adaptive resistance of a plastic genome," Cell Mol. Life Sci., Nov. 2005, pp. 2617-2633, vol. 62, No. 22, Birkhauser Verlag, Basel.
Fuda, C. et al., "The Basis for Resistance to beta-Lactam Antibiotics by Penicillin-binding Protein 2a of Methicillin-resistant *Staphylococcus aureus*," J. Biol. Chem., Sep. 24, 2004, pp. 40802-40806, vol. 279, No. 39.
GenBank AP003139.1, "*Staphylococcus aureus* subsp. *aureus* N315 plasmid pN315 DNA," Oct. 7, 2016, 15 pgs.
GenBank BA000018.3, "*Staphylococcus aureus* subsp. *aureus* N315 DNA," Oct. 7, 2016, 636 pgs.
Goldstein, F. et al., "Identification and Phenotypic Characterization of a beta-Lactam-Dependent, Methicillin-Resistant *Staphylococcus aureus* Strain," Antimicrobial Agents and Chemotherapy, Jul. 2007, pp. 2514-2522, vol. 51, No. 7.
Gonzales, P. et al., "Synergistic, collaterally sensitive triple beta-lactam combinations against MRSA suppress resistance in vitro and

(56) References Cited

OTHER PUBLICATIONS clear infection in vivo," HHS Public Access Author Manuscript, available in PMC May 1, 2016, pp. 1-26, published in final edited form as: Nat. Chem. Biol., Nov. 2015, pp. 855-861, vol. 11, No. 11.
Gu, B. et al., "The emerging problem of linezolid-resistant *Staphylococcus*," J. Antimicrob. Chemother., 2013, pp. 4-11, vol. 58, Oxford University Press.
Hackbarth, C. et al., "blaI and blaR1 Regulate beta-Lactamase and PBP2a Production in Methicillin-Resistant *Staphylococcus aureus*," Antimicrobial Agents and Chemotherapy, May 1993, pp. 1144-1149, vol. 37, No. 5.
Harris, P. et al., "Meropenem versus piperacillin-tazobactam for definitive treatment of bloodstream infections due to ceftriaxone non-susceptible *Escherichia coli* and *Klebsiella* spp (the MERINO trial): study protocol for a randomised controlled trial," Trials, 2015, pp. 1-8, vol. 16, No. 24.
Harrison, E. et al., "A novel hybrid SCCmec-mecC region in *Staphylococcus sciuri*," J. Antimicrob. Chemother., 2014, pp. 911-918, vol. 69.
Hegreness, M. et al., "Accelerated evolution of resistance in multidrug environments," PNAS, Sep. 16, 2008, pp. 13977-13981, vol. 105, No. 37.
Imamovic, L. et al., "Use of Collateral Sensitivity Networks to Design Drug Cycling Protocols That Avoid Resistance Development," Sci. Transl. Med., Sep. 25, 2013, pp. 1-10, vol. 5, No. 204, 204ra132.
International Search Report and Written Opinion dated Sep. 16, 2016 from related PCT Patent Application No. PCT/US2016/041565; 9 pgs.
Kinzig, M. et al., "Pharmacokinetics and Tissue Penetration of Tazobactam and Piperacillin in Patients Undergoing Colorectal Surgery," Antimicrobial Agents and Chemotherapy, Sep. 1992, pp. 1997-2004, vol. 36, No. 9.
Koga, T. et al., "Affinity of Tomopenem (CS-023) for Penicillin-Binding Proteins in *Staphylococcus aureus*, *Escherichia coli*, and *Pseudomonas aeruginosa*," Antimicrobial Agents and Chemotherapy, Mar. 2009, pp. 1238-1241, vol. 53, No. 3.
Kumar, K. et al., "Molecular docking and molecular dynamics studies on beta-lactamases and penicillin binding proteins," Mol. BioSyst., 2014, pp. 891-900, vol. 10, The Royal Society of Chemistry.
Kumarasamy, K. et al., "Emergence of a new antibiotic resistance mechanism in India, Pakistan, and the UK: a molecular, biological, and epidemiological study," Lancet Infect. Dis., Sep. 2010, pp. 597-602, vol. 10.

Kuroda, M. et al., "Whole genome sequencing of meticillin-resistant *Staphylococcus aureus*," Lancet, Apr. 21, 2001, pp. 1225-1240, vol. 357, No. 9264.
Lazar, V. et al., "Bacterial evolution of antibiotic hypersensitivity," Mol. Syst. Biol., 2013, pp. 1-12, vol. 9, No. 700, Macmillan Publishers Limited.
Lee, S. et al., "Antagonism of Chemical Genetic Interaction Networks Resensitize MRSA to beta-Lactam Antibiotics," Chem. Biol., Nov. 23, 2011, pp. 1379-1389, vol. 18, Elsevier Ltd.
Lehar, J. et al, "High-order combination effects and biological robustness," Mol. Syst. Biol., 2008, pp. 1-6, vol. 4, No. 215, Nature Publishing Group.
Li, H. et al., "The Sequence Alignment/Map format and SAMtools," Bioinformatics, 2009, pp. 2078-2079, vol. 25, No. 16.
Long, S. et al., "PBP2a Mutations Causing High-Level Ceftaroline Resistance in Clinical Methicillin-Resistant *Staphylococcus aureus* Isolates," Antimicrobial Agents and Chemotherapy, Nov. 2014, pp. 6668-6674, vol. 58, No. 11.
Lowy, F., "Antimicrobial resistance: the example of *Staphylococcus aureus*," J. Clin. Invest., May 2003, pp. 1265-1273, vol. 111, No. 9.
Malouin, F. et al., "Modification of Penicillin-Binding Proteins as Mechanisms of Beta-Lactam Resistance," Antimicrobial Agents and Chemotherapy, Jul. 1986, pp. 1-5, vol. 30, No. 1.
"Merrem IV (meropenem for injection), for intravenous use," AstraZeneca Pharmaceuticals, L.P., 2013, 7 pgs.
Munck, C. et al., "Prediction of resistance development against drug combinations by collateral responses to component drugs," Sci. Transl. Med., Nov. 12, 2014, pp. 1-12, vol. 6, No. 262, 262ra156.
Nascimento, T. et al., "Potential spread of multidrug-resistant coagulase-negative staphylococci through healthcare waste," J. Infect. Dev. Ctries., 2015, pp. 29-34, vol. 9, No. 1.
Extended European Search Report dated Nov. 7, 2018 from related European Patent Application No. 16822054.9; 10 pgs.
Lim, D. et al., "Structural basis for the beta-lactam resistance of PBP2a from methicillin-resistant *Staphylococcus aureus*," Nat. Structural Biol., Nov. 2002, pp. 870-876, vol. 9, No. 11, Nature Publishing Group.
Ozseven, A. et al., "Do Different Interpretative Methods Used for Evaluation of Checkerboard Synergy Test Affect the Results?," Mikrobiyol. Bul., 2012, pp. 410-420, vol. 46, No. 3.
Sumita, Y. et al., "In Vitro Synergistic Activity between Meropenem and Other Beta-Lactams against Methicillin-Resistant *Staphylococcus aureus*," Euro. J. Clinical Microbiol. Infect. Diseases, Jan. 1991, pp. 77-84, vol. 10, No. 2, Springer, Wiesbaden, Germany.

\* cited by examiner

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 1
cgtgccgaaa tcaatgaaag acgc                                    24

<210> SEQ ID NO 2
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 2
ggcaccttca gaaccaaatc cacc                                    24

<210> SEQ ID NO 3
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 3
tggaacgatg cctatctcat atgc                                    24

<210> SEQ ID NO 4
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 4
caggaatgca gaaagaccaa agc                                     23

<210> SEQ ID NO 5
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 5
tttatcagca accttatagt cttttggaac                              30

<210> SEQ ID NO 6
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 6
cctgctgctt tcggcaagac                                         20

<210> SEQ ID NO 7
<211> LENGTH: 24
<212> TYPE: DNA
<213> ORGANISM: Artificial Sequence

```
<220> FEATURE:
<223> OTHER INFORMATION: SYNTHESIZED

<400> SEQUENCE: 7
cgatgtggat ggagcgcata ttag                                              24

<210> SEQ ID NO 8
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 8
acaacggtgg ctgtgcaata tac                                               23
```

COMPOSITIONS AND METHODS OF USE OF ANTIBACTERIAL DRUG COMBINATIONS

CROSS REFERENCE TO RELATED APPLICATIONS

This application claims the benefit of U.S. Provisional Application No. 62/190,588, filed Jul. 9, 2015, and PCT Application number PCT/US/2016/041565, filed Jul. 8, 2016, the disclosures of which are hereby incorporated by reference in their entirety.

GOVERNMENTAL RIGHTS

This invention was made with government support under DK098089, GM099538, AI090818, AI104987, GM007067, and HG000045 awarded by the National Institutes of Health and DGE1143954 awarded by the National Science Foundation. The government has certain rights in the invention.

FIELD OF THE INVENTION

The disclosure relates to antibacterial compositions and methods of treating bacterial infections caused by resistant bacteria.

BACKGROUND OF THE INVENTION

Multidrug-resistant (MDR) pathogens represent a growing threat to human health, with many infectious diseases effectively regressing toward the pre-antibiotic era, exemplified by the dramatic rise of community-acquired methicillin-resistant *Staphylococcus aureus* (MRSA) infections. Methicillin-resistant *Staphylococcus aureus* (MRSA) is one of the most prevalent multidrug-resistant pathogens worldwide, exhibiting increasing resistance to the latest antibiotic monotherapies used to treat these infections. The emergence of MRSA has virtually eliminated the use of β-lactams as therapeutic options against *S. aureus*. The recently developed β-lactam agent ceftaroline, which exhibits activity in treatment of MRSA infections, does so by binding to the allosteric site of PBP2a, triggering opening of the active site for inactivation by the drug; however, resistance to ceftaroline and other antibiotics used to treat MRSA, including linezolid, vancomycin, and daptomycin, has been reported. Thus, there is a need in the art for a new strategy to treat MDR pathogens and repurpose existing antibiotics.

SUMMARY OF THE INVENTION

In an aspect, the disclosure provides a composition useful for the treatment of an infection caused be an antibiotic resistant bacterium, wherein the resistance is due to a penicillin-binding protein 2a (PBP2a)-driven mechanism. The composition comprises: (i) at least one carbapenem or other suitable β-lactam capable of binding the allosteric site of PBP2a; (ii) at least one β-lactamase inhibitor; and (iii) at least one β-lactam that binds the open configuration of the active site of PBP2a. In certain embodiments, the antibiotic resistant bacterium is methicillin-resistant *Staphylococcus aureus* (MRSA). In one embodiment, the carbapenem is meropenem, the β-lactamase inhibitor is tazobactam and the β-lactam that binds the open configuration of the active site of PBP2a is piperacillin. In another embodiment, the carbapenem is imipenem, the β-lactamase inhibitor is clavulanate and the β-lactam that binds the open configuration of the active site of PBP2a is piperacillin. In still another embodiment, the carbapenem is meropenem, the β-lactamase inhibitor is tazobactam and the β-lactam that binds the open configuration of the active site of PBP2a is amoxicillin. Specifically, the composition suppresses the evolution of resistance to the composition.

In another aspect, the disclosure provides a method for treating an infection caused by an antibiotic resistant bacterium in a subject, wherein the resistance is due to a penicillin-binding protein 2a (PBP2a)-driven mechanism. The method comprises administering to the subject an effective amount of a composition of the disclosure.

In still another aspect, the disclosure provides a method for treating an infection caused by methicillin-resistant *Staphylococcus aureus* (MRSA). The method comprises administering to the subject an effective amount of a composition of the disclosure.

BRIEF DESCRIPTION OF THE FIGURES

The application file contains at least one drawing executed in color. Copies of this patent application publication with color drawing(s) will be provided by the Office upon request and payment of the necessary fee.

(FIG. 3A) MRSA N315 interaction network of collateral sensitivities and resistance between ME/PI/TZ, its single and double constituents, and other 13-lactam compounds of various sub-classes (cephalosporins, penicillins, carbapenems, and 13-lactamase inhibitors). Node colors indicate sub-classes of 13-lactams, 13-lactamase inhibitors, or combinations. Blue arrows indicate collateral sensitivities. Black lines indicate collateral resistance. For example, adaptation to piperacillin sensitizes MRSA N315 to meropenem and imipenem. Cephalosporins were not collaterally sensitive to any of the compounds we tested. Where pairs were not tested or no collateral effects were seen, no connecting arrows are shown. (FIG. 3B) MRSA N315 interaction network of collateral sensitivities and resistance between ME/PI/TZ and its single and double constituents only. Bold blue arrows indicate reciprocal collateral sensitivities between two nodes, e.g., piperacillin and meropenem/tazobactam.

(FIG. 4A) Adaptation of MRSA N315 to meropenem/tazobactam or tazobactam alone destabilizes plasmid pN315. Read coverage aligning to pN315 in MRSA N315 adapted to drug combinations containing tazobactam (TZ) or not containing tazobactam (non-TZ), versus total reads per sample. Days of adaptation under the given conditions are indicated, e.g., D-2 indicates isolate was sequenced after two days of adaptation. (FIG. 4B, FIG. 4C) qRT-PCR confirms disregulation of the bla and mec operons as causative mechanisms of some collateral sensitivities in MRSA N315. Expression of blaZ or mecA shown relative to gyrB in wild-type MRSA N315 or adapted strains (N315 adapted to TZ 100 µg/ml, and PI 33.3 or 100 µg/ml), subsequently grown in broth-only or broth+sub-MIC PI or TZ. N.D.=Not determined. "-" indicates no expression. Loss of blaZ expression in MRSA N315 adapted to TZ confirms loss of blaZ and the bla operon, and is consistent with disregulation of mecA expression. Data are from three replicate experiments. Error bars indicate standard error of measurement.

(FIG. 6A, FIG. 6B, FIG. 6C) pbp2a/mecA antisense (AS) strain. Targeted repression of PBP2a showed increased susceptibility for meropenem when under xylose induction. Increased susceptibility was also observed for piperacillin. Increased susceptibility was observed for all combinations. (FIG. 6D, FIG. 6E) pbpA antisense (AS) strain. Targeted repression of PBP1 showed increased susceptibility to meropenem and piperacillin. Increased susceptibility was observed for the ME/PI, ME/TZ, and ME/PI/TZ combinations. (FIG. 6F, FIG. 6G) pbp2 antisense (AS) strain. Targeted repression of PBP2 showed increased susceptibility to meropenem and piperacillin. Increased susceptibility was observed for all combinations. (FIG. 6H, FIG. 6I) pbp3 antisense (AS) strain. Targeted repression of PBP3 showed no increase in susceptibility to any of the single drugs. A slight increase in susceptibility was observed for the ME/PI combination; no change in susceptibility was observed for any of the other combinations.

DETAILED DESCRIPTION OF THE INVENTION

Figure 1:
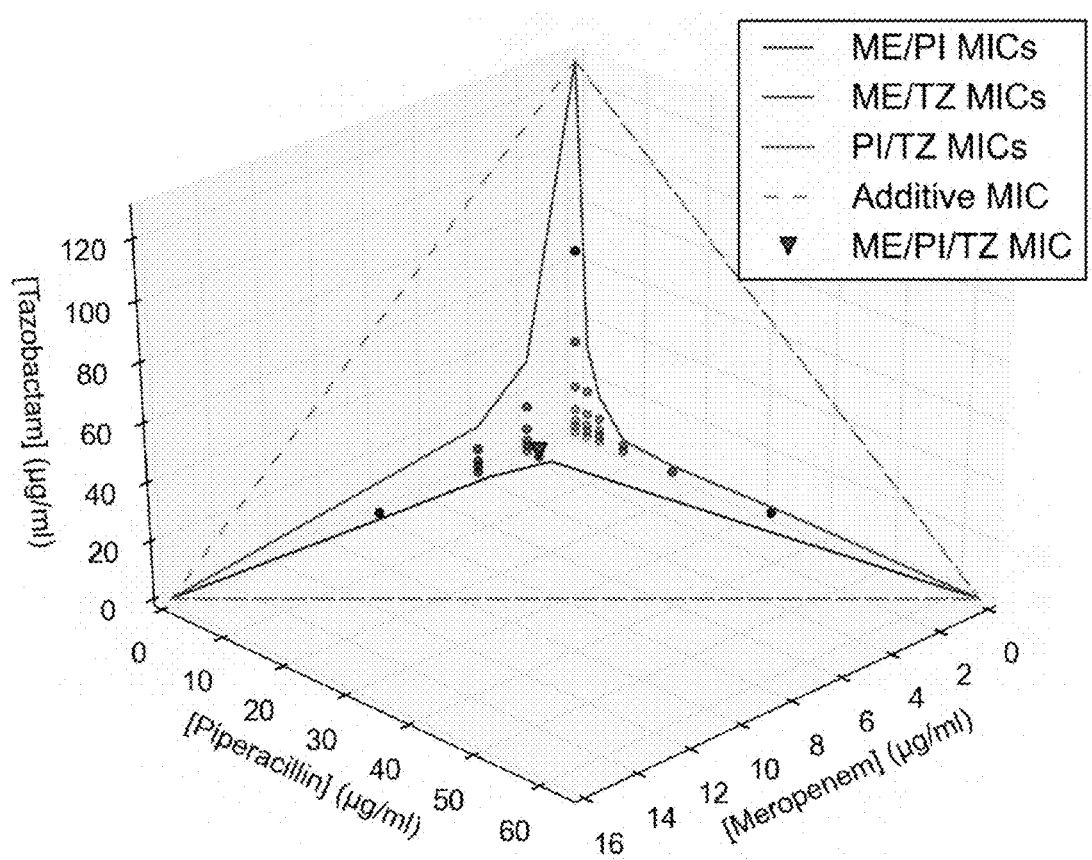
FIG. 1 depicts a 3D-checkerboard synergy determination showing isoboles of minimal inhibitory concentrations (MIC) and in vitro grown in single-, double-, or triple-drug conditions of ME/PI/TZ. Colored lines/isoboles within each panel indicate MICs of two drugs in combination. Dashed lines indicate theoretical concentrations of additive interactions. Points indicate top sub-inhibitory concentrations of meropenem (ME), piperacillin (PI) and tazobactam (TZ) for each tested condition. The red triangle indicates the MIC of all three drugs in combination (Each at 2 μg/ml).

Disclosed herein are compositions comprising a combination of antibiotics from three subclasses of β-lactam antibiotics, all targeting cell-wall synthesis. This therapy uses: 1) antibiotics that target multiple nodes in the same cellular system, 2) combinations of these antibiotics that increase drug potency by utilizing drug synergy, and 3) collateral sensitivity between constituents of the combination to suppress resistance evolution. Without wishing to be bound by theory, the composition comprises a carbapenem or other suitable β-lactam which inhibits penicillin-binding protein 1 (PBP1) and allosterically opens the active site of PBP2a for inhibition by another molecule of antibiotic in the combination, a β-lactam that binds PBP2 and PBP2a, and a β-lactamase inhibitor the protects the β-lactam(s) from β-lactamases. This culminates in a synergistic response by simultaneous perturbation of multiple components of the cell-wall synthesis machinery. The inventors have shown that the combination acts synergistically and is bactericidal against bacteria comprising PBP2a, specifically methicillin-resistant Staphylococcus aureus (MRSA).

I. Compositions

In an aspect, provided herein are composition useful for the treatment of an infection caused be an antibiotic resistant bacterium, wherein the resistance is due to a penicillin-binding protein 2a (PBP2a)-driven mechanism. The composition comprises at least one carbapenem or other suitable β-lactams capable of binding the allosteric site of PBP2a; at least one β-lactamase inhibitor; and at least one β-lactam that binds the open configuration of the active site of PBP2a.

The inventors have discovered that the disclosed composition reduces or eliminates the evolution of resistant bacteria following exposure to the recited combination of antibiotics. In the disclosed composition, it is essential that one antibiotic bind the allosteric site of PBP2a and that another antibiotic binds the active site of PBP2a. Without wishing to be bound by theory, the antibiotic that binds the allosteric site of PBP2a opens the transpeptidase active site of PBP2a such that the antibiotic that binds the active site of PBP2a may also bind to a separate site on PBP2a. Binding of both these antibiotics is required to completely stop the vital transpeptidase function of PBP2a. By stopping the transpeptidase function of PBP2a, an antibiotic resistant bacterium that relies on a PBP2a-driven mechanism for resistance will be killed. One specific example of such a bacterium is methicillin-resistant *Staphylococcus aureus* (MRSA). The β-lactamase inhibitor of the composition further facilitates killing of the resistant bacteria by protecting the β-lactam(s) in the combination from enzymatic breakdown by β-lactamases produced by the resistant bacteria.

According to the disclosure, the composition is effective against antibiotic-resistant bacteria, wherein the resistance is due to a penicillin-binding protein 2a (PBP2a)-driven mechanism. A skilled artisan would be able to determine if the antibiotic-resistant bacteria exhibits resistance due to a PBP2a-driven mechanism. For example, the bacteria may comprise mecA, which encodes for PBP2a. Generally, species within the genus *Staphylococcus* are known to possess the mecA gene at this time, including: *S. aureus, S. epidermidis, S. hominis, S. lugdunensis, S. xylosus*, and *S. felis* (Petinaki et al. Detection of mecA, mecR1 and mecI genes among clinical isolates of methicillin-resistant staphylococci by combined polymerase chain reactions. J. Antimicrob. Chemother. 47, 297-304 (2001)), (Nascimento et al. Potential spread of multidrug-resistant coagulase-negative staphylococci through healthcare waste. J. Infect. Dev. Ctries. 9, (2015)). Accordingly, in an embodiment, an antibiotic-resistant bacterium is from the genus *Staphylococcus*. In another embodiment, an antibiotic-resistant bacterium is selected from the group consisting of *S. aureus, S. epidermidis, S. hominis, S. lugdunensis, S. xylosus*, and *S. felis*. In a specific embodiment, the antibiotic-resistant bacterium is methicillin-resistant *Staphylococcus aureus* (MRSA). PBPs are penicillin-binding proteins, which are the transpeptidase enzymes necessary for synthesis of the peptidoglycan cell wall in bacteria. There are four native PBPs in *Staphylococcus aureus*, of which PBP2 is the essential PBP for viability of the cell. In addition to possessing PBP2, methicillin-resistant *S. aureus* (MRSA) has acquired an accessory PBP (PBP2a) that is able to perform all critical transpeptidase activity for cell wall synthesis. PBP2a has transpeptidase activity even in the presence of many β-lactams which typically function by inhibiting the native PBP2. The β-lactam drugs specifically target PBPs, and are composed of several subclasses which all contain the β-lactam "warhead", have varying PBP affinities. Non-limiting examples include the penicillins, carbapenems, cephalosporins, and monobactams. However, PBP2a has poor binding affinity with some of the β-lactams while it is in its native, closed conformation, resulting in high resistance to this drug class by PBP2a-containing organisms. Accordingly, the present disclosure overcomes this poor binding by employing one β-lactam that binds to the allosteric site of PBP2a thus keeping it open while a second β-lactam binds to the open configuration of the active site thereby effectively inhibiting the function of PBP2a.

A composition of the disclosure comprises, in part, a carbapenem or other suitable β-lactams capable of binding the allosteric site of PBP2a. Accordingly, a carbapenem or suitable β-lactam of the disclosure must bind to the allosteric site of PBP2a. Non-limiting examples of carbapenems or β-lactams that bind to the allosteric site of PBP2a include meropenem, imipenem, tomopenem, ceftaroline and ceftobiprole. In a specific embodiment, the carbapenem is selected from the group consisting of meropenem and imipenem. In another specific embodiment, the carbapenem is meropenem. In still another specific embodiment, the carbapenem is imipenem.

A composition of the disclosure comprises, in part, a β-lactamase inhibitor. A suitable β-lactamase inhibitor protects the β-lactam also present in the composition from enzymatic breakdown by β-lactamases produced by the bacteria. Accordingly, a β-lactamase inhibitor inhibits the activity of β-lactamases, a family of enzymes that break the β-lactam ring that allows penicillin-like antibiotics to work. Non-limiting examples of β-lactamase inhibitors include clavulanic acid (clavulanate), sulbactam, tazobactam, and avibactam. In a specific embodiment, the β-lactamase inhibitor is selected from the group consisting of tazobactam and clavulanate. In another specific embodiment, the β-lactamase inhibitor is tazobactam. In still another specific embodiment, the β-lactamase inhibitor is clavulanate.

A composition of the disclosure comprises, in part, a β-lactam that binds the open configuration of the active site of PBP2a. Accordingly, a β-lactam of the disclosure must bind to the open configuration of the active site of PBP2a. Non-limiting examples of β-lactams that bind to the open configuration of the active site of PBP2a include carbapenems, aminopenicillins, carboxypenicillins, ureidopenicillins, oxacillins, methicillins, and some cephalosporins. Non-limiting examples of carbapenems include meropenem, imipenem, doripenem, ertapenem, faropenem, and tebipenem. Non-limiting examples of oxacillins and methicillins include cloxacillin, dicloxacillin, flucloxacillin, oxacillin, methicillin and nafcillin. Non-limiting examples of cephalosporins that bind to the open configuration of the active site of PBP2a include cefepime, cefozopran, cefpirome, cefquinome, ceftaroline, and ceftobiprole. Notably, most penicillin-type β-lactams (e.g. aminopenicillins, carboxypenicillins, ureidopenicillins) bind to the open configuration of the active site of PBP2a. Non-limiting examples of aminopenicillins include amoxicillin, ampicillin, pivampicillin, hetacillin, bacampicillin, metampicillin, talampicillin, and epicillin. Non-limiting examples of carboxypenicillins include carbenicillin, carindacillin, ticarcillin and temocillin. Non-limiting examples of ureidopenicillins include azlocillin, mezlocillin and piperacillin. Specific non-limiting examples of β-lactams that do not bind to the open configuration of the active site of PBP2a and will not work in a composition of the disclosure include mecillinam, cefradine and thienamycin. In a specific embodiment, the β-lactam that binds the open configuration of the active site of PBP2a is selected from the group consisting of piperacillin and amoxicillin. In another specific embodiment, the β-lactam that binds the open configuration of the active site of PBP2a is piperacillin. In still another specific embodiment, the β-lactam that binds the open configuration of the active site of PBP2a is amoxicillin.

In a specific embodiment, the carbapenem or other suitable β-lactam capable of binding the allosteric site of PBP2a is meropenem, the β-lactamase inhibitor is tazobactam and the β-lactam that binds the open configuration of the active site of PBP2a is piperacillin. In another specific embodiment, the carbapenem or other suitable β-lactam capable of binding the allosteric site of PBP2a is imipenem, the β-lactamase inhibitor is clavulanate and the β-lactam that binds the open configuration of the active site of PBP2a is piperacillin. In still another specific embodiment, the carbapenem or other suitable β-lactam capable of binding the allosteric site of PBP2a is meropenem, the β-lactamase inhibitor is tazobactam and the β-lactam that binds the open configuration of the active site of PBP2a is amoxicillin.

The ratio of the amount of each antibiotic in the combination may be experimentally determined via methods known in the art. For example, a 3-D checkerboard graph may be used to determine the ratio of each antibiotic in the combination as depicted in FIG. 1. Using such a methodology, a skilled artisan may be able to determine the optimal ratio of the antibiotic combination. As demonstrated by the inventors, the ratio of the antibiotics in the combination may range from 64:1:1, 1:64:1, and 1:1:64 to 1:1:1. In a specific embodiment, the ratio of carbapenem or other suitable β-lactam capable of binding the allosteric site of PBP2a to β-lactamase inhibitor to β-lactam that binds the open configuration of the active site of PBP2a is 1:1:1. However, it is understood that these ratios may be varied and still result in an effective combination of the disclosure.

Advantageously, a composition of the disclosure suppresses the evolution of resistance to said composition. Often patients treated with a specific antibiotic development resistance to said antibiotic due to various reasons. The development and spread of resistance can dramatically dampen the effectiveness and longevity of antimicrobial therapy. Surprisingly, the inventors have shown that a combination of the disclosure suppresses the evolution of resistance. Stated another way, after prolonged exposure of the bacteria to a combination of the disclosure, no bacteria resistant to said combination were observed. This is in stark contrast to both single drug and dual drug combinations.

(a) Pharmaceutical Composition

The present disclosure also provides pharmaceutical compositions. The pharmaceutical composition comprises one or more antibiotics of the disclosure, as an active ingredient, and at least one pharmaceutically acceptable excipient.

The pharmaceutically acceptable excipient may be a diluent, a binder, a filler, a buffering agent, a pH-modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

II. Methods

In an aspect, the present disclosure encompasses a method for treating an infection caused by an antibiotic resistant bacterium in a subject, wherein the resistance is due to a penicillin-binding protein 2a (PBP2a)-driven mechanism. The method comprises administering to the subject an effective amount of a composition of the disclosure.

In another aspect, the present disclosure encompasses a method for treating an infection caused by methicillin-resistant *Staphylococcus aureus* (MRSA). The method comprises administering to the subject an effective amount of a composition of the disclosure.

The term "infection" as used herein includes presence of microbes, including bacteria, in or on a subject, which, if its growth were inhibited, would result in a benefit to the subject. As such, the term "infection" in addition to referring to the presence of bacteria also refers to normal flora which, are not desirable. The term "infection" includes infection caused by bacteria.

The term "treat", "treating" or "treatment" as used herein refers to administering a pharmaceutical composition of the disclosure for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering a composition of the disclosure, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infections, or (iv) suppress the clinical manifestation of a bacterial infection, or (v) suppress the manifestation of adverse symptoms of the bacterial infections.

The term "control" or "controlling" as used herein generally refers to preventing, reducing, or eradicating infection or inhibiting the rate and extent of such infection, or reducing the microbial population, such as a microbial population present in or on a body or structure, surface, liquid, subject, etc, wherein such prevention or reduction in the infection or microbial population is statistically significant with respect to untreated infection or population. In general, such control may be achieved by increased mortality amongst the microbial population.

The term "effective amount" as used herein refers to an amount, which has a therapeutic effect or is the amount required to produce a therapeutic effect in a subject. For example, a therapeutically or pharmaceutically effective amount of an antibiotic agent or a pharmaceutical composition is the amount of the antibiotic agent or the pharmaceutical composition required to produce a desired therapeutic effect as may be judged by clinical trial results, model animal infection studies, and/or in vitro studies (e.g. in agar or broth media). The effective or pharmaceutically effective amount depends on several factors, including but not limited to, the microorganism (e.g. bacteria) involved, characteristics of the subject (for example height, weight, sex, age and medical history), severity of infection and the particular type of the antibiotic used. For prophylactic treatments, a therapeutically or prophylactically effective amount is that amount which would be effective to prevent a microbial (e.g. bacterial) infection. Notably, the combination disclosed herein may allow for effective amount of the combination of active agents to be lower than the effective amount alone such that a lower total concentration of antibiotic is administered to a subject.

The term "administration" or "administering" includes delivery of a composition or one or more pharmaceutically active ingredients to a subject, including for example, by any appropriate methods, which serves to deliver the composition or it's active ingredients or other pharmaceutically active ingredients to the site of the infection. The method of administration can vary depending on various factors, such as for example, the components of the pharmaceutical composition or the type/nature of the pharmaceutically active or inert ingredients, the site of the potential or actual infection, the microorganism involved, severity of the infection, age and physical condition of the subject. Some non-limiting examples of ways to administer a composition or a pharmaceutically active ingredient to a subject according to this disclosure includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, the compositions or active ingredients thereof are administered orally.

The compositions according to the disclosure can be formulated into various dosage forms wherein the active ingredients may be present either together (e.g. as an admixture) or as separate components. When the various ingredients in the composition are formulated as a mixture, such composition can be delivered by administering such a mixture (e.g. in the form of a suitable unit dosage form such as tablet, capsule, solution, powder etc.). Alternatively, the ingredients may also be administered separately (simultaneously or one after the other) as long as these ingredients reach beneficial therapeutic levels such that the composition as a whole provides a synergistic effect. The composition or dosage form wherein the ingredients do not come as a mixture, but come as separate components, such composition/dosage form can be administered in several ways. In one possible way, the ingredients can be mixed in the desired proportions and the mixture is then administered as required. Alternatively, the components can be separately administered in appropriate proportions so as to achieve the same or equivalent therapeutic level or effect as would have been achieved by administration of the equivalent mixture.

A subject may be a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc.

In general, the pharmaceutical compositions and method disclosed herein are useful in treating or controlling bacterial infections caused by antibiotic resistant bacteria, wherein the resistance is due to a penicillin-binding protein 2a (PBP2a)-driven mechanism. Some non-limiting examples of such bacteria known to have developed resistance due to PBP2a include *S. aureus, S. epidermidis, S. hominis, S. lugdunensis, S. xylosus*, and *S. felis* (Petinaki et al. Detection of mecA, mecR1 and mecI genes among clinical isolates of methicillin-resistant staphylococci by combined polymerase chain reactions. J. Antimicrob. Chemother. 47, 297-304 (2001)), (Nascimento et al. Potential spread of multidrug-resistant coagulase-negative staphylococci through healthcare waste. J. Infect. Dev. Ctries. 9, (2015)). In a specific embodiment, the antibiotic resistant bacterium is methicillin-resistant *Staphylococcus aureus* (MRSA). Non-limiting examples of infections that may be prevented or treated using the compositions and/or methods of the disclosure include: skin and soft tissue infections, febrile neutropenia, urinary tract infection, intraabdominal infections, respiratory tract infections, pneumonia (nosocomial), bacteremia meningitis, and surgical infections.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

Multidrug-resistant (MDR) pathogens represent a growing threat to human health, with many infectious diseases effectively regressing toward the pre-antibiotic era[1-3], exemplified by the dramatic rise of community-acquired methicillin-resistant *Staphylococcus aureus* (MRSA) infections. In the 1940's, *S. aureus* infections were primarily treated with first-generation β-lactams (penicillins), which target the penicillin-binding proteins (PBPs), the critical transpeptidases for cell-wall synthesis[4]. Four PBPs (PBP1-PBP4) perform these functions in *S. aureus*[4]. Emergence of β-lactamase-producing strains led to development of β-lactamase-resistant second-generation penicillins, including methicillin. Soon after the introduction of methicillin in 1959, the first MRSA strains were reported[5]. These strains acquired a highly regulated collection of genes from a non-*S. aureus* source that produced inducible resistance to β-lactam antibiotics[4]. One of these genes, mecA, encodes penicillin-binding protein 2a (PBP2a). PBP2a performs the critical transpeptidase reaction that cross-links the cell wall, even under challenge by β-lactam antibiotics, when other PBPs are inhibited[6-8]. The mechanistic basis for this outcome is complex, involving a closed conformation for the active site, whose function is regulated by allostery[9,10]. The emergence of MRSA has virtually eliminated the use of β-lactams as therapeutic options against *S. aureus*. The recently developed β-lactam agent ceftaroline, which exhibits activity in treatment of MRSA infections, does so by binding to the allosteric site of PBP2a, triggering opening of the active site for inactivation by the drug[10,11]; however, resistance to ceftaroline[12] and other antibiotics used to treat MRSA, including linezolid, vancomycin, and daptomycin, has been reported[13-15].

Use of multidrug combination therapy targeting orthogonal cellular processes has been successful in treating *Mycobacterium tuberculosis, Helicobacter pylori*, and other infections[16,17]. However, resistance is increasing even against these therapies[15-20]. We have identified a new potential therapy against MRSA consisting of a combination of clinically approved drugs from three distinct generations and subclasses of β-lactam antibiotics, all targeting cell-wall synthesis: meropenem, piperacillin, and tazobactam (ME/PI/TZ). This therapy uses elements from three strategies: 1) use of semi-synthetic antibiotic derivatives that target multiple nodes in the same cellular system[12,21], 2) use of combinations of these antibiotics that increase drug potency by utilizing drug synergy[22,23], and 3) use of collateral sensitivity between constituents of the combination to suppress resistance evolution[24,25]. Each of these methods have been successfully employed against the major MDR Gram-negative and Gram-positive human pathogens[26,27]. However, these strategies used individually have often been thwarted by the evolution of new resistance in MDR pathogens, leading to diminishing options for treating their infections[5,14,21,28,29].

We hypothesize that ME/PI/TZ operates through inhibition of PBP1 by meropenem, the targeting of PBP2 by piperacillin, protection of piperacillin from the PC1 class A β-lactamases by tazobactam[6,30-34], and allosteric opening of the active site of PBP2a by meropenem for inhibition by another molecule of antibiotic in the combination[11]. This culminates in a synergistic response by simultaneous perturbation of multiple components of the cell-wall synthesis machinery in MRSA. We find that exposure of MRSA N315 to the components of ME/PI/TZ reveals reciprocal collateral sensitivities within this highly synergistic triple combination that suppress the evolution of resistance, in contrast to some synergistic combination therapies that instead accelerate resistance evolution[23,35]. This effect is consistent with recent work showing that collateral sensitivity slows evolution of resistance in a non-pathogenic laboratory strain of *Escherichia coli*[24,36]. Our results support renewed clinical use of older β-lactam antibiotics against MRSA when used in synergistic combinations of collaterally sensitive components, opening a new treatment paradigm with existing drugs that are already approved for human use.

Example 1. Synergy Between Meropenem, Piperacillin, and Tazobactam in MRSA Strains In Vitro Based on its high level of resistance against 23 diverse antibiotics (Table 1), *S. aureus* MRSA N315[37] was selected from a group of fully genome-sequenced MDR strains of MRSA for this study. MRSA N315 contains the staphylococcal chromosome cassette mec (SCCmec) type II encoding the mec methicillin-resistance operon[38], as well as penicillinase plasmid pN315 containing the bla β-lactamase operon[39]. From a focused combinatorial screen of these 23 antibiotic compounds, including representatives from every major drug class (Table 1), we identified the combination of ME/PI/TZ to display highly synergistic, bactericidal activity against MRSA N315 in vitro, using the metric of the fractional inhibitory concentration index (FICI), FICI=0.11[40,41] (Table 2A). For any number of drugs in combination, a FICI less than 1 indicates synergy, a FICI equal to 1 indicates additivity, and a FICI greater than 1 indicates indifference or antagonism[40,41]. Notably, these three drugs all belong to different sub-classes of the β-lactam drugs, which target the critical transpeptidase enzymes of cell-wall synthesis, though MRSA strains are typically highly resistant to most β-lactams[8]. The general resistance to individual β-lactams results from the inability of these drugs to inhibit the transpeptidase active site of PBP2a, which compensates for β-lactam inhibition of the other transpeptidases in *S. aureus*[8].

ME/PI/TZ exhibits increased synergy against MRSA N315 relative to its three constituent double combinations meropenem/piperacillin (ME/PI), meropenem/tazobactam (ME/TZ) and piperacillin/tazobactam (PI/TZ) at clinically relevant concentrations (FIG. 1, Table 2B-C). All three β-lactam compounds were tested for final MIC and FICI using a 3-D checkerboard with twofold dilution series of each compound from 128-to-2 µg/ml, and no-drug. These allowed up to a 64-fold difference in component ratios to be explored for maximal synergy, as well as allowing for isolation of results for each single compound, all constituent double combinations, and the triple combination. Using the 3-D checkerboard, we determined the optimal ratio for ME/PI/TZ to be 1:1:1 for minimal drug input and maximal synergy against MRSA N315. The minimal-inhibitory concentrations (MICs) of the three components in the combination against MRSA N315 (2 µg/ml each) are below the clinical susceptibility breakpoints for each of these drugs alone against methicillin-susceptible *S. aureus* (4-8 µg/ml)[42]. The constituent double combinations ME/PI and PI/TZ are also synergistic against N315 with FICI=0.44 and 0.22, respectively, while ME/TZ is less synergistic at 0.67. Based on the Loewe additivity model of synergy, drugs cannot be synergistic with themselves[36]. Though the β-lactams all target the cell-wall pathway, our use of the FICI method (Loewe additivity) confirms the non-additive nature of these interactions. In contrast to the high synergy of ME/PI/TZ seen in MRSA N315, the combination exhibits slightly less than additive activity (FICI=1.12) in the methicillin-susceptible *S. aureus* (MSSA) reference strain ATCC 29213[42,43] (Table 2B-C), and we hypothesize the necessity of PBP2a for synergy to occur.

We propose that the mechanism of synergy observed for ME/PI/TZ results from allosteric triggering of PBP2a by its constituents, akin to that reported for ceftaroline[10,11]. Indeed, we determined that meropenem binds to the allosteric site of PBP2a with a dissociation constant ($K_d$) of 270±80 µM (equivalent to 104±31 µg/ml). The mean peak plasma concentration in healthy humans after a bolus intravenous injection of meropenem at the recommended 1 g dose is 112 µg/ml[44]. The concentrations of meropenem achieved clinically are above the $K_d$; thus at these concentrations meropenem binding to the allosteric site of PBP2a would trigger opening of the active site of PBP2a, enabling access to its transpeptidase active site for acylation/inactivation either by another molecule of meropenem or by other β-lactams in the combination[8,10,45].

The highly synergistic activity of ME/PI/TZ against MRSA N315 was recapitulated against all in a panel of 72 clinical MRSA isolates with multiple SCCmec types represented (Table 3A-B). The MIC of the combination against the clinical isolates ranged from 0.4-33.3 µg/ml for each component, with a mean of 9.7 µg/ml, and an $MIC_{50}$ and $MIC_{90}$ of 3.7 µg/ml and 33.3 µg/ml, respectively (Table 4A).

Example 2. Mechanistic Robustness of Synergy Using Alternate Carbapenems, Penicillins, and β-Lactamase Inhibitors Against MRSA We determined that the observed synergy is not limited to the antibiotics assayed, but can be generalized to their respective β-lactam classes, by testing MRSA N315 and representative clinical MRSA isolates against other carbapenem/penicillin/β-lactamase inhibitor combinations. We found that treatment of MRSA N315 with imipenem/piperacillin/clavulanate (IM/PI/CV) shows equal or greater synergism to ME/PI/TZ. Meropenem/amoxicillin/tazobactam (ME/AX/TZ) maintains high synergy in MRSA N315 only (FICI=0.04), with clinical MRSA isolate showing less synergy (FICI=0.55) (Table 2B). MICs for components of these substituted triples are all below the mean peak human plasma concentrations of these in vivo[46,47]. Similar to ME/PI/TZ, IM/PI/CV shows less-than-additive activity against MSSA ATCC 29213 (FICI=1.14) (Table 2B-C).

These results further support the necessity of the presence of the mecA gene product PBP2a with its attendant allosterism for synergy, due to lack of synergy of carbapenem/penicillin/β-lactamase inhibitor combinations in methicillin-susceptible S. aureus.

We also tested the effect of replacing the carbapenem component of the combination with either a monobactam or a cephalosporin, two other later-generation β-lactam derivatives. In contrast to ME/PI/TZ, the triple combinations aztreonam/piperacillin/tazobactam (AZ/PI/TZ) and cefepime/piperacillin/tazobactam (CP/PI/TZ) (FICI for both=0.33) have lower levels of synergy than PI/TZ alone (FICI=0.22) (Table 2B), possibly because aztreonam (a monobactam) has Gram-negative PBP activity[48], while cefepime (a cephalosporin) preferentially targets PBP2 over PBP1[8].

Figure 6A:
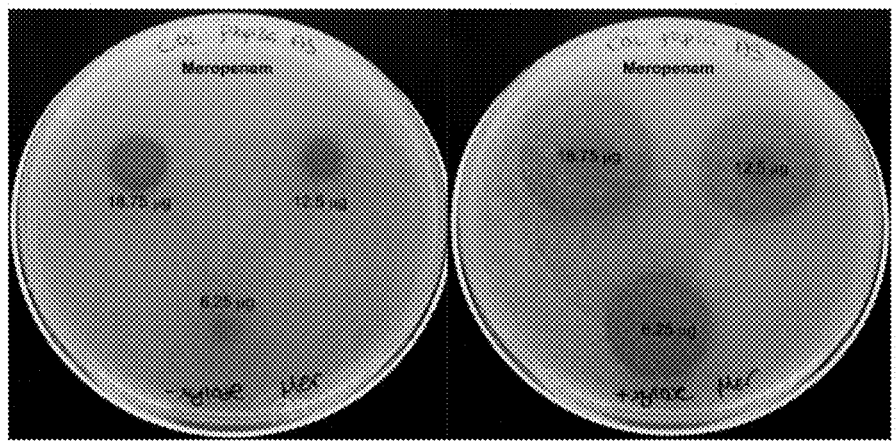
FIG. 6A, FIG. 6B, FIG. 6C, FIG. 6D, FIG. 6E, FIG. 6F, FIG. 6G, FIG. 6H and FIG. 6I depict bacterial plate growth illustrating PBP xylose induction for MRSA COL antisense (AS) strains.
Figure 6B:
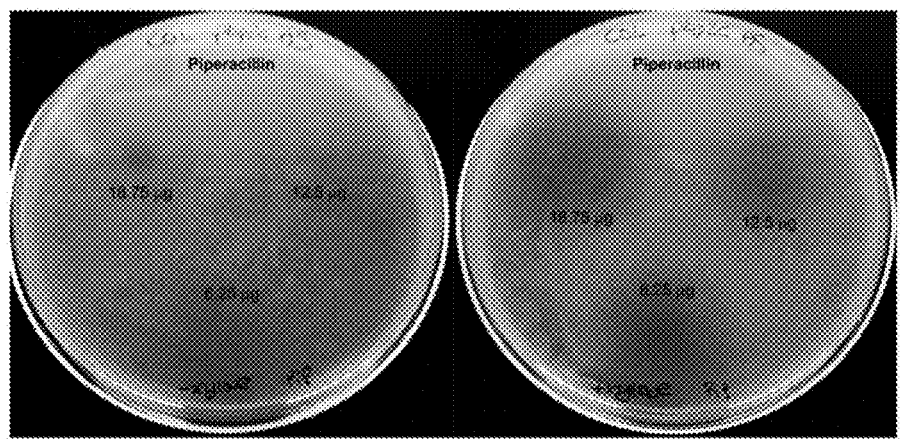
Figure 6C:
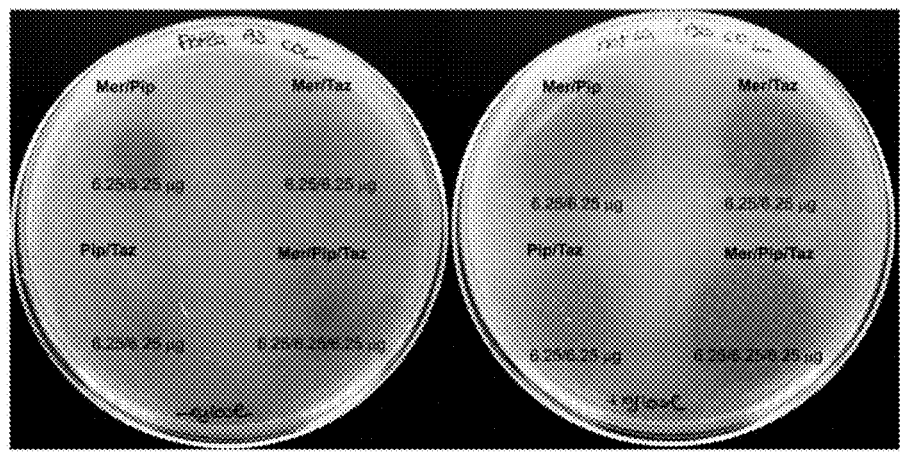
Figure 6D:
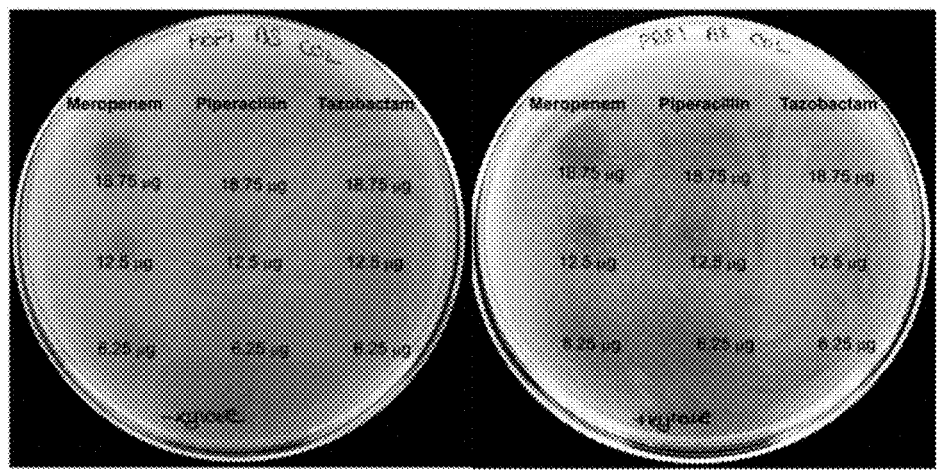
Figure 6E:
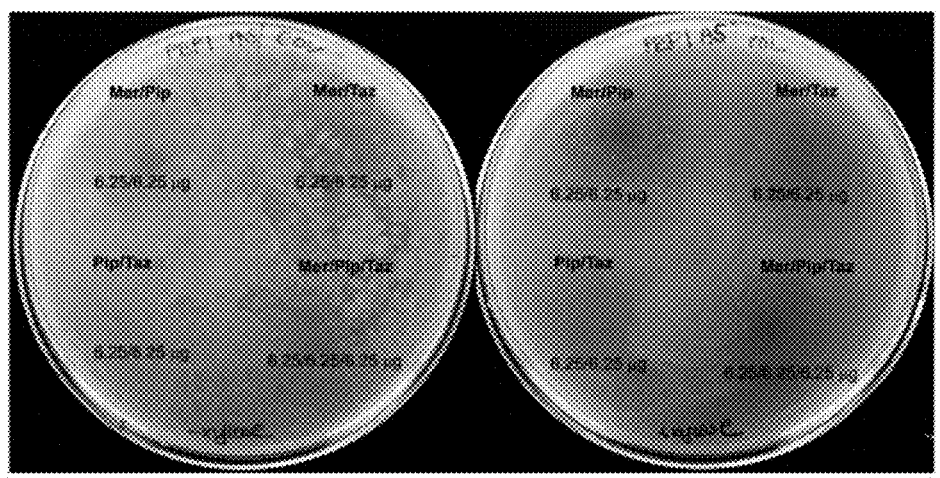
Figure 6F:
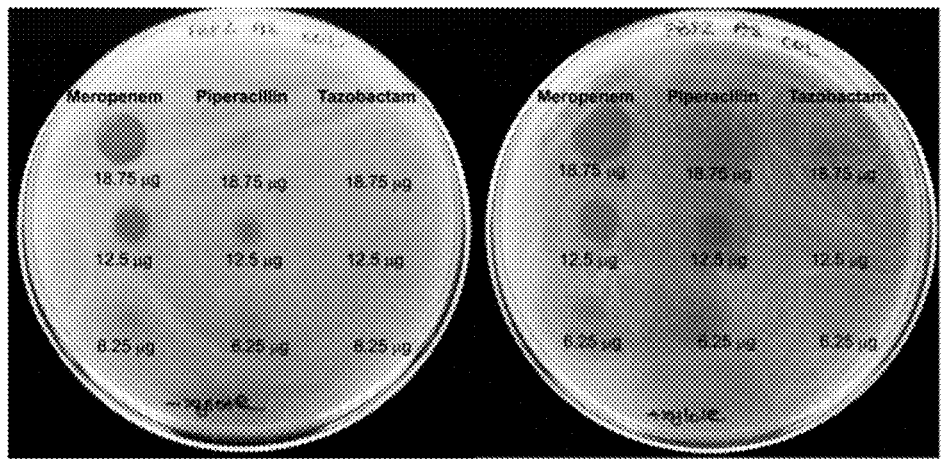
Figure 6G:
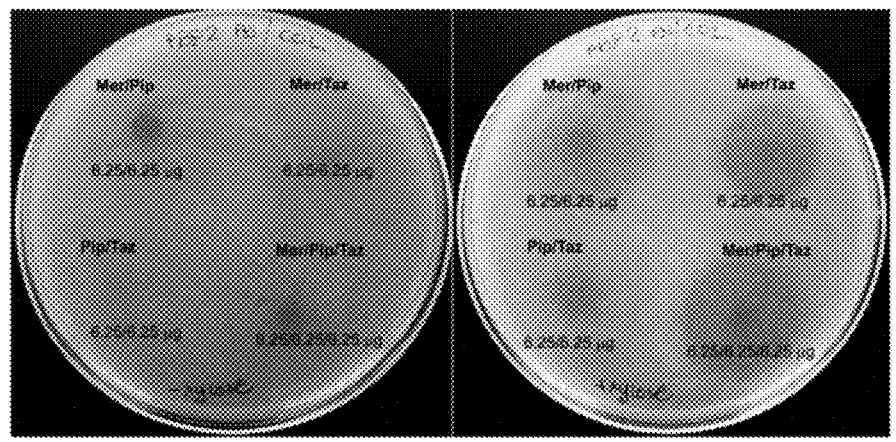
Figure 6H:
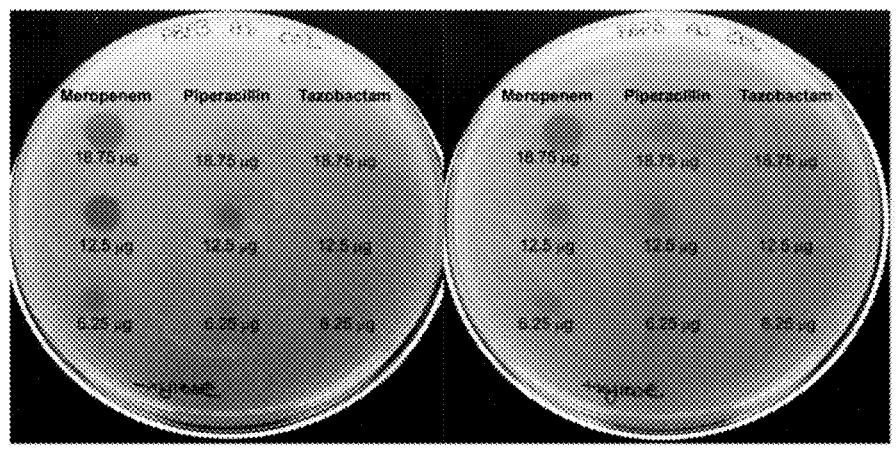
Figure 6I:
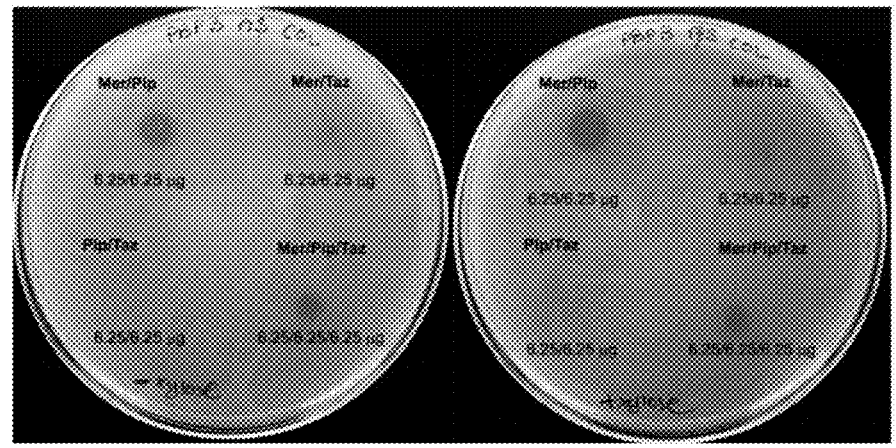

We confirmed the targets of the constituents of ME/PI/TZ by reducing the expression of PBP1, PBP2, PBP2a or PBP3 using a xylose-inducible antisense-RNA strategy in the MRSA COL strain background[49]. When expression levels of PBP2a were attenuated, the strain behaved as a methicillin-susceptible S. aureus and was sensitized to all tested β-lactams (FIG. 6A-C). When meropenem, piperacillin, and tazobactam were tested against the pbpA antisense strain, only meropenem showed larger zones of inhibition under xylose induction, confirming PBP1 as a target of meropenem (FIG. 6D-E). For the pbp2 antisense strain both meropenem and piperacillin showed increased effectiveness under xylose induction, demonstrating that they each have some activity against PBP2 (FIG. 6F-G). We did not observe any effect with the pbp3 antisense strain, consistent with our hypothesis that ME/PI/TZ activity is focused on disrupting PBP1, PBP2, and PBP2a (FIG. 6H-I). The antisense strains in all cases but that of pbp3 showed sensitization to the triple combination, underscoring the observed synergy.

Example 3. Lack of Adaptation to Meropenem/Piperacillin/Tazobactam Over >10 Days for MRSA N315

Figure 2:
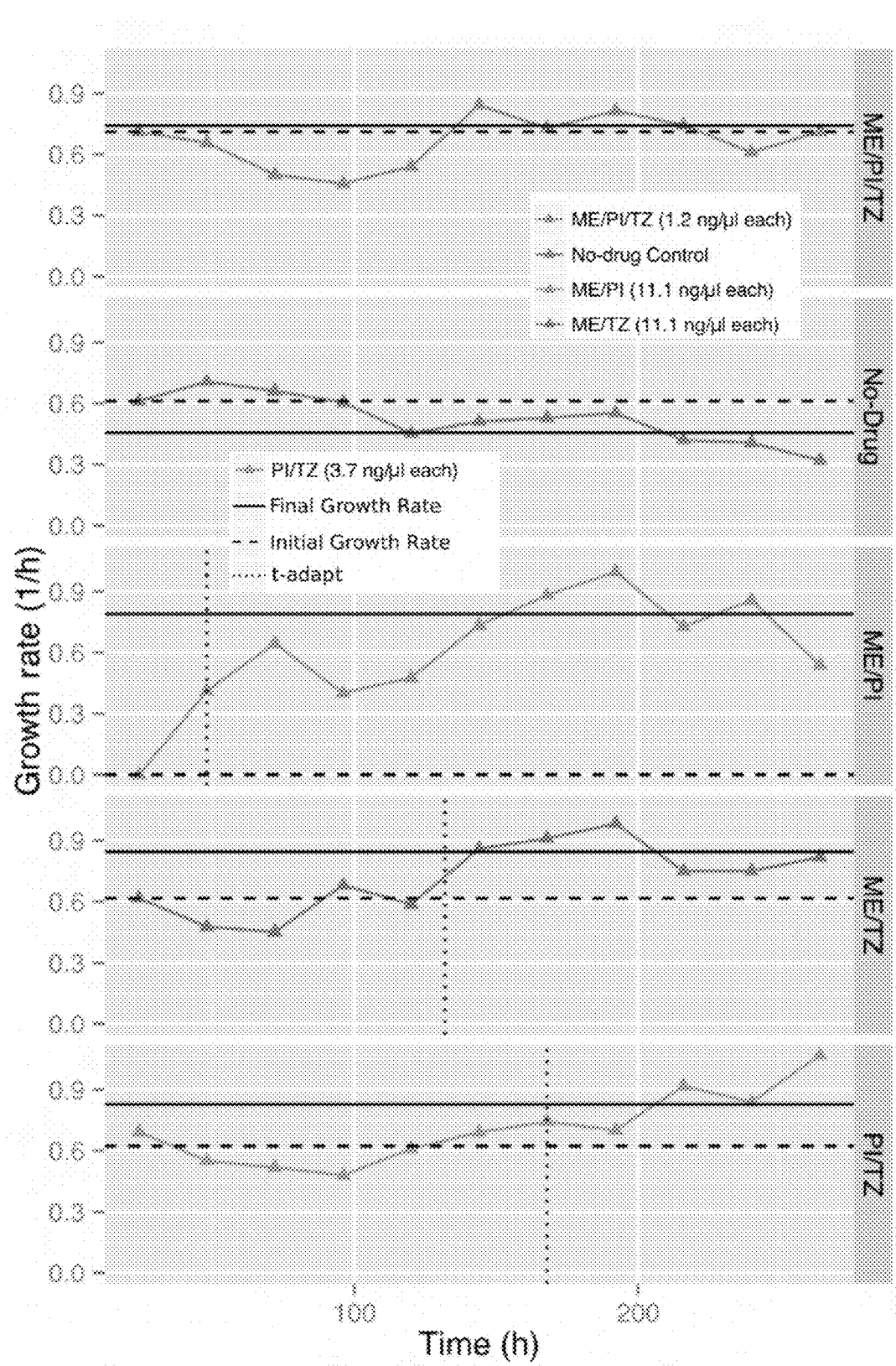
FIG. 2 depicts a graph displaying the change in growth rates over time of MRSA N315 when challenged with antibacterial combinations. Growth rates of MRSA N315 over an 11-day period were computed for each antibacterial combination tested at one threefold dilution below MIC. The differences in growth rate (Δr) between day one (Initial Growth Rate) and the averaged rate of the last six days of the assay (Final Growth Rate) were calculated. MRSA N315 in conditions whose change in growth rate Δr>0.2 were considered to be adapted. The adaptation time parameter t-adapt was calculated as the time at which change in growth rate was half-maximal. Adaptation rate, $\alpha=(\Delta r/2)/t\text{-adapt}$ $(1/h^2)$, was computed for strains meeting this criterion. Results are from two replicate experiments. rate for ME/PI: $\alpha=8.23\times10^{-3}$ $h^{-2}$; ME/TZ: $\alpha=8.68\times10^{-4}$ $h^{-2}$; PI/TZ: $\alpha=4.32\times10^{-3}$ $h^{-2}$. Only ME/PI/TZ at one threefold dilution below MIC (1.2 μg/ml each) and No-drug Control displayed lack of increase in growth rate and were non-adapted.

Development and spread of resistance can dramatically dampen the effectiveness and longevity of an antimicrobial therapy. We demonstrated that ME/PI/TZ suppresses the evolution of resistance in MRSA using serial passaging in sub-inhibitory antibiotic concentrations of the triple combination and each of its constituents. To more accurately model a clinical treatment in vitro and in vivo, we applied these drugs at fixed dosages over extended periods as occurs in clinical treatment, not at increasing doses over time. During the 11-day experiment, we observed no evolution of resistance in MRSA N315 to ME/PI/TZ. In contrast, we observed resistance evolution against all double combinations and single constituents within 1-8 days, consistent with prior work[23,50] (FIG. 2). Viable cells were observed in all conditions above the initially determined MIC for the doubles and singles, but not for those conditions at or above the initial MIC for ME/PI/TZ. Increases in growth rates over time were noted in all doubles and singles, while the growth rate of N315 in sub-MIC ME/PI/TZ over time was unchanged throughout the experiment, equivalent to the no-drug control (FIG. 2)[23]. Also, N315 exposed to the double combination ME/PI showed a threefold increase in MIC after day one, indicating that viable cells were present after day one, but did not grow until further passage and adaptation. Determination of the minimal-bactericidal concentration (MBC) confirmed that the triple combination ME/PI/TZ is bactericidal against MRSA N315 (Table 4B). Together, these results demonstrate the suppression of emergence of new resistance against ME/PI/TZ in MRSA N315.

Figure 3A:
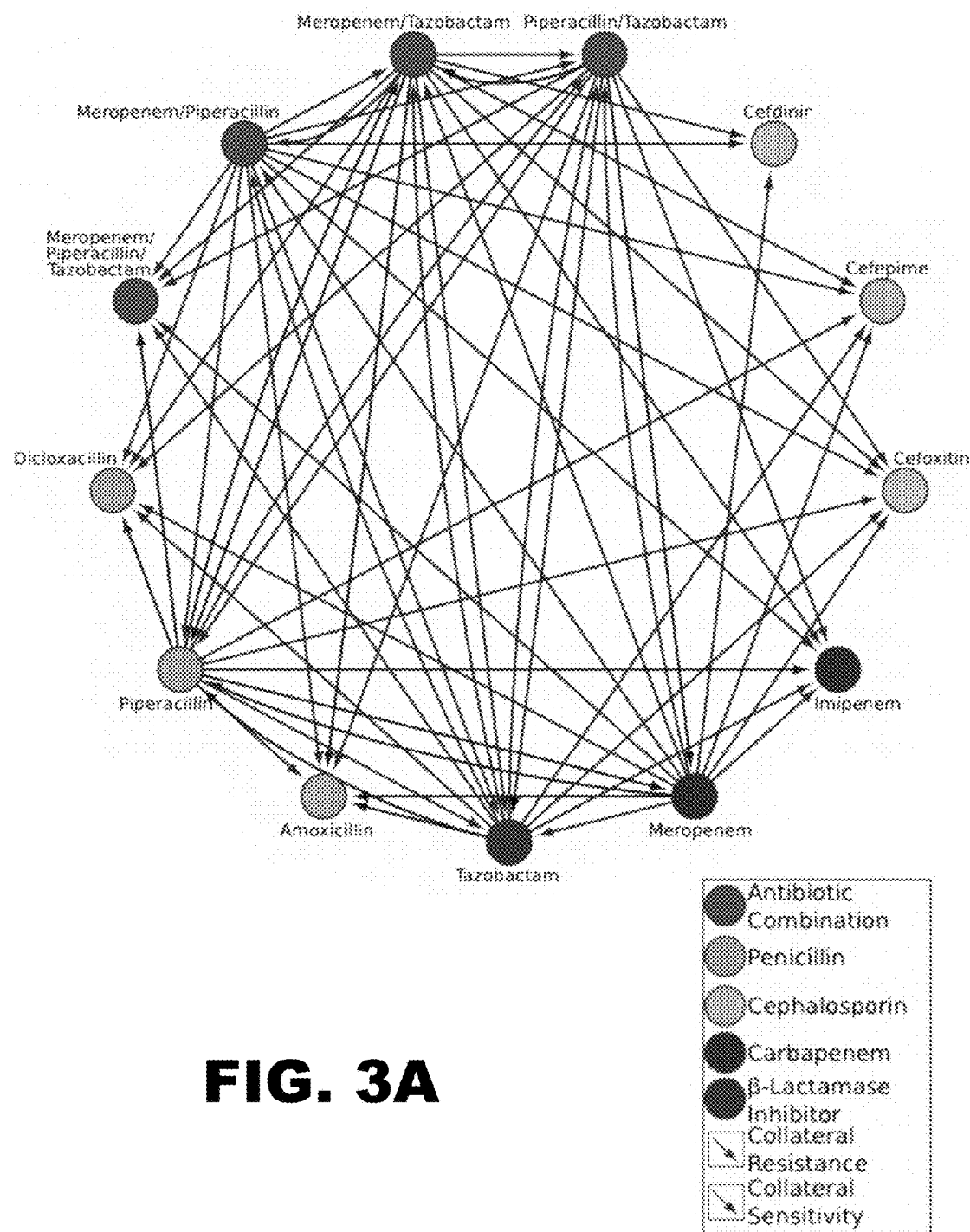
FIG. 3A and FIG. 3B depict diagrams illustrating the collateral sensitivities that underlie suppression of adaptation to antibacterial combinations in MRSA N315.
Figure 3B:
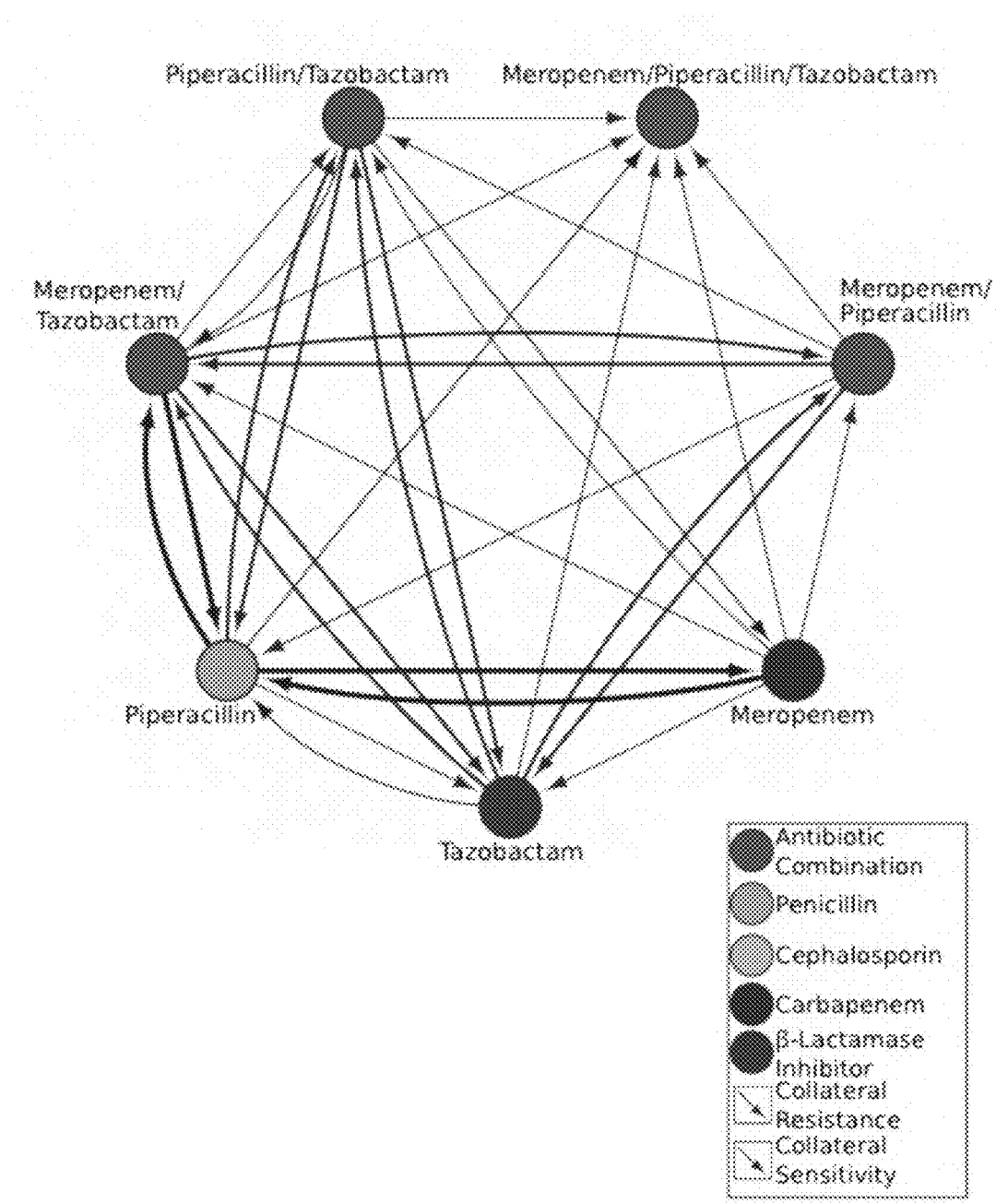
Figure 7:
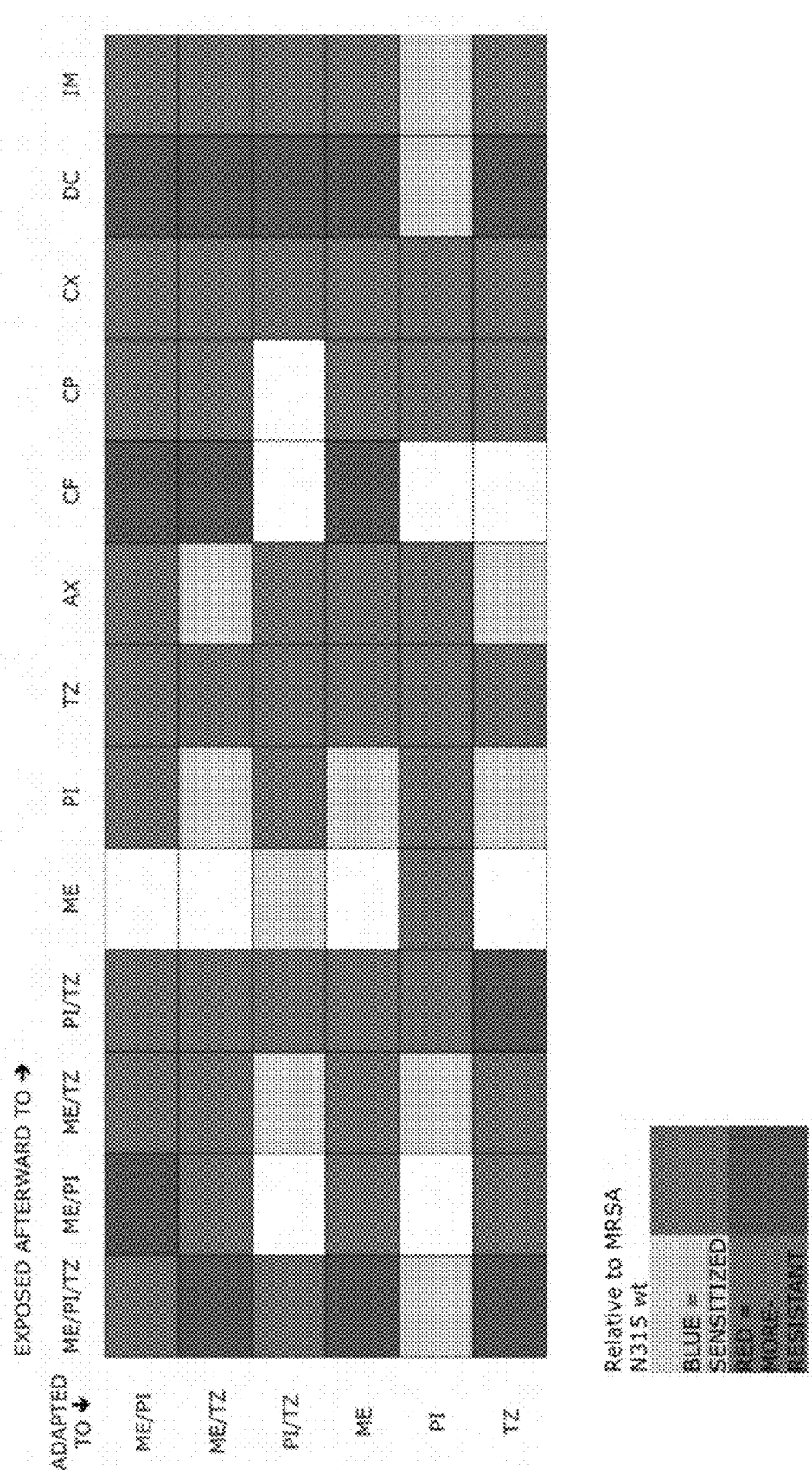
FIG. 7 depicts a plot illustrating collateral sensitivities underlying the suppression of adaptation to β-lactam combinations in MRSA N315. Blue shades indicate collateral sensitization of strain to single drugs and combinations, after prior adaptation to single and double drug combinations. Red shades indicate collateral resistance. Light shading=change of one MIC dilution. Dark shading=change of two or more MIC dilutions. For example, adaptation to piperacillin yields collateral sensitivity to meropenem, and vice versa. ME=meropenem, PI=piperacillin, TZ=tazobactam, AX=amoxicillin, CF=cefdinir, CP=cefepime, CX=cefoxitin, DC=dicloxacillin, IM=imipenem.

Example 4. Reciprocal Collateral Sensitivities of Components of these Combinations Underlie Suppression of Adaptation To determine whether collateral sensitivity was a factor in the suppression of adaptation of ME/PI/TZ, we analyzed the effects of prior exposure of MRSA N315 to a range of β-lactams on susceptibility to the other components (FIG. 3 and FIG. 7). We observed that there was strong reciprocal collateral sensitivity between meropenem and piperacillin, and between piperacillin and ME/TZ, while PI/TZ sensitized MRSA N315 to meropenem, but not reciprocally. Collateral sensitivity to piperacillin was also conferred by prior exposure to tazobactam, but not vice-versa. Interestingly, no collateral sensitivity was found to tazobactam after exposure to any other single or double compounds. Collateral sensitivity and resistance profiles of amoxicillin and piperacillin are nearly identical, with adaptation to meropenem also sensitizing MRSA N315 to amoxicillin (FIG. 3 and FIG. 7). Piperacillin also showed collateral sensitization to imipenem, an even more potent carbapenem against MRSA N315. However, none of the cephalosporins tested for collateral sensitivity by the carbapenem/penicillin/β-lactamase inhibitor combinations or constituents resulted in sensitivity, but rather increased resistance or indifference was noted. These results confirm that the observed suppression of resistance by collateral sensitivity is specific to the constituent drug classes of M E/PI/TZ.

Example 5. Adapted MRSA N315 Undergoes Large-Scale Genomic Alterations

Figure 4A:
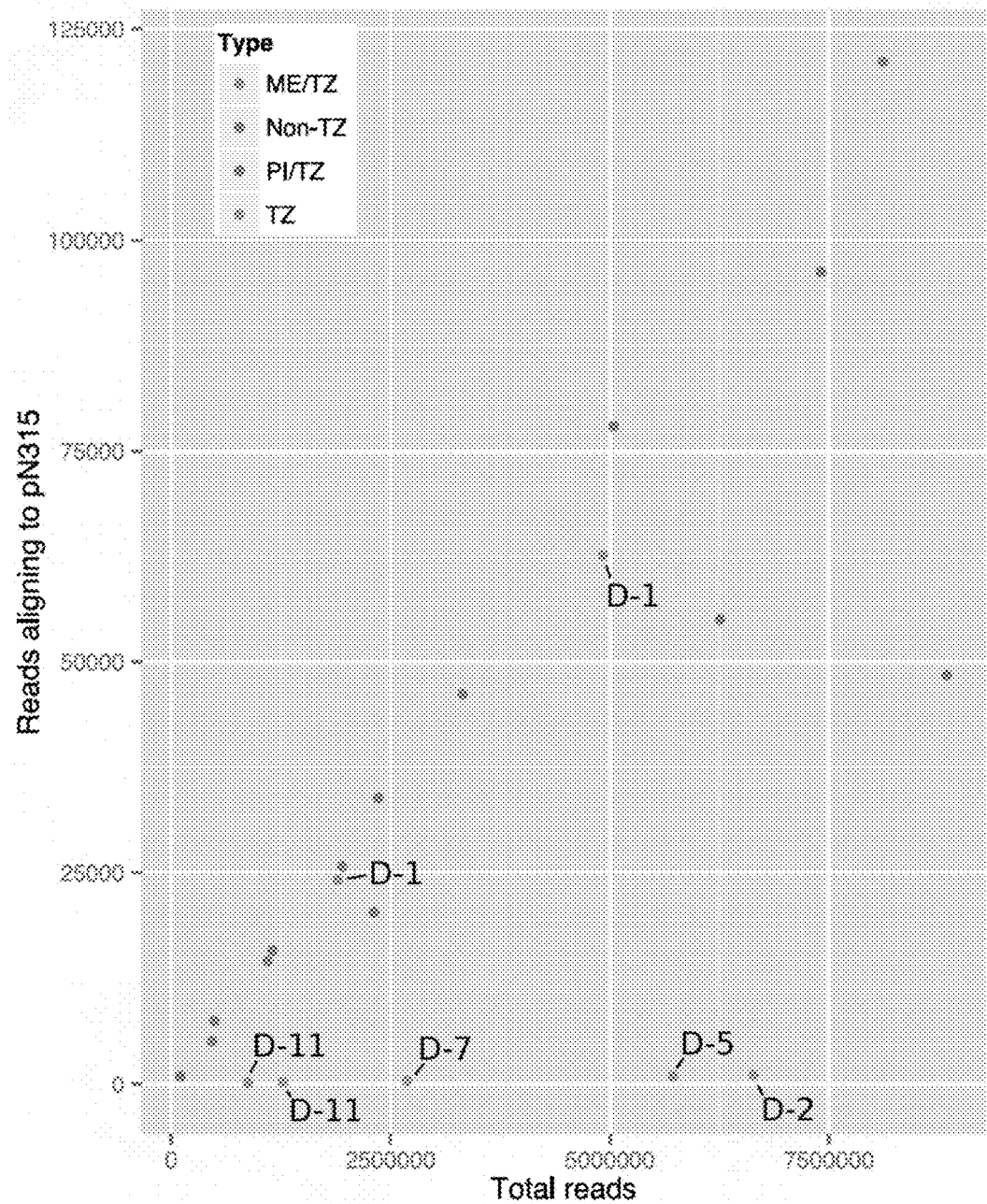
FIG. 4A, FIG. 4B and FIG. 4C depict graphs showing genomic evidence for mechanisms of synergy and collateral sensitivity.
Figure 8:
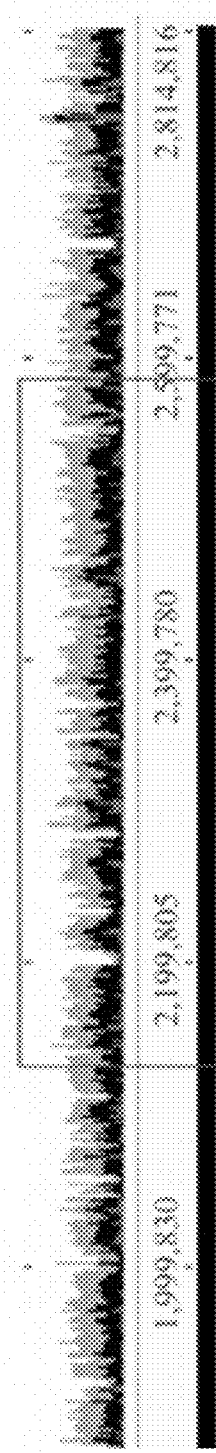
FIG. 8A, FIG. 8B, FIG. 8C and FIG. 8D depict histograms illustrating the genomic duplication in MRSA N315 adapted to piperacillin/tazobactam. Histogram showing the total read coverage across the genome of N315 adapted to FIG. 8A, meropenem/tazobactam for five days, FIG. 8B, tazobactam alone for two days, FIG. 8C, piperacillin/tazobactam for six days, and FIG. 8D, piperacillin/tazobactam for 11 days. Average per-base read coverage across the entire genome and only in the region indicated by the red box are, respectively: a) 116.6 reads/bp and 126.6 reads/bp; b) 124.5 reads/bp and 128.9 reads/bp; c) 157.8 reads/bp and 302.2 reads/bp; and d) 120.1 reads/bp and 230.6 reads/bp. Clones in FIG. 8A and FIG. 8B were chosen to be representative of all non-piperacillin/tazobactam adaptations.

We used whole-genome sequencing to investigate the genomic basis of the sensitivity and resistance phenotypes of wild-type and adapted MRSA N315 strains. We found no mutations in PBP or β-lactamase genes within any of the adapted MRSA N315 isolates. However, absence of read coverage identified that the penicillinase plasmid pN315 was lost in isolates adapted to tazobactam-only (100 μg/ml) and ME/TZ (11.1 μg/ml each) (FIG. 4A). This plasmid loss occurred much more rapidly than with previously reported techniques for curing plasmids from MRSA, such as high heat and SDS treatment[51]. In PI/TZ adapted isolates, we observed that approximately 400 kb of the MRSA N315 chromosome (GenBank ID: BA000018.3) was duplicated after analysis of read coverage depth, from approximate genomic positions 2,100,000 to 2,550,000 bp. Interestingly, this interval contains several putative and confirmed genes involved in cell-wall synthesis, including ddlA D-Ala-D-Ala ligase (FIG. 8).

Figure 4B:
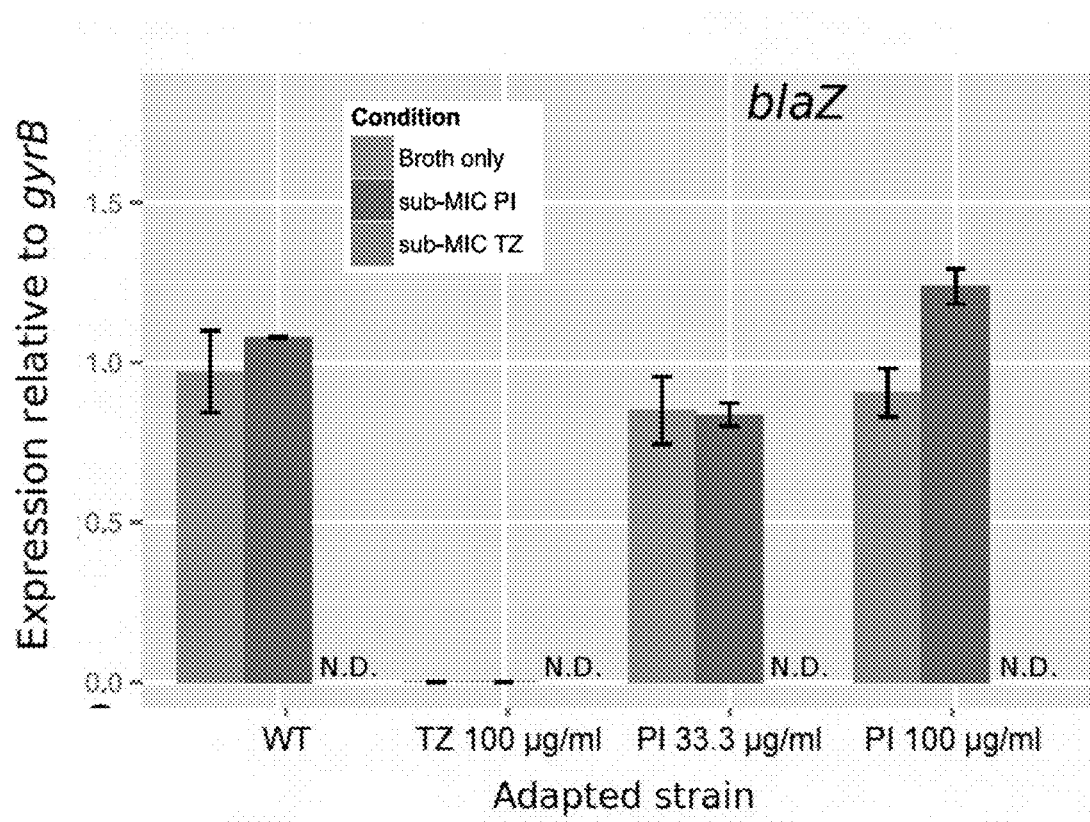
Figure 4C:
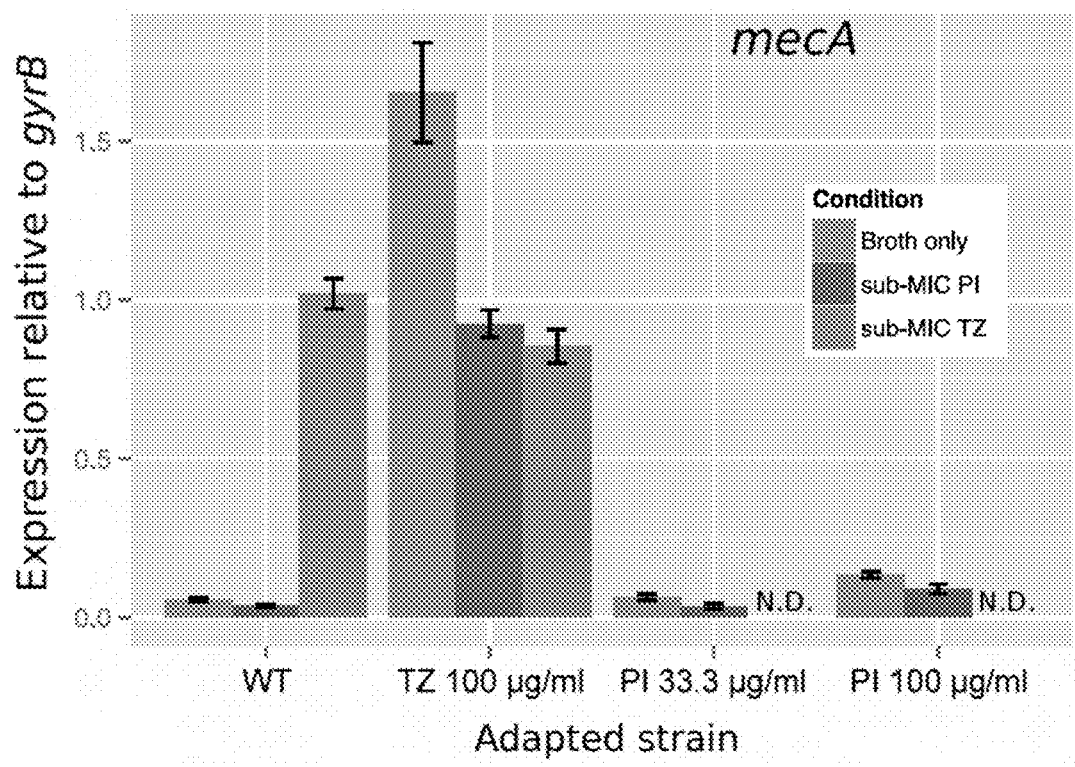

The loss of pN315 in MRSA N315 correlates with increased sensitivity to piperacillin and amoxicillin, both penicillins that should be sensitive to the blaZ (PC1) class A β-lactamase encoded on the plasmid. However, the loss of pN315 also results in increased resistance to tazobactam-only and ME/PI/TZ (FIG. 3, FIG. 7, Table 5A). One possible link between the presence of pN315 and ME/PI/TZ activity is the known regulatory crosstalk between MecI and BlaI repressors and their shared mec operon target[52-54]. To test the effect of the loss of pN315 on expression of genes known to be important for ME/PI/TZ activity, we performed qRT-PCR analysis of the adapted and wild-type MRSA N315 strains (FIG. 4B). We determined that expression of the blaZ β-lactamase in the pN315 plasmid within wild-type MRSA N315 is constitutive, but in clones adapted to tazobactam we saw no expression of blaZ, consistent with loss of pN315 in these clones. We also found that expression of mecA is constitutive in the blaZ-null MRSA N315 isolate that was adapted to tazobactam at 100 µg/ml, consistent with disregulation of the mec operon via loss of pN315 and the bla operon. Finally, we found tazobactam to be a strong inducer of mecA in wild-type MRSA N315, at levels similar to the constitutive expression of mecA seen in the blaZ-null condition.

Example 6. Synergy of ME/PI/TZ when MRSA N315 has Evolved Resistance to Constituents We then examined the role that resistance to components of ME/PI/TZ has on its effectiveness against MRSA (Table 5A). Previous exposure of MRSA N315 to piperacillin at either 33.3 or 100 µg/ml showed subsequent sensitization of the strain to ME/PI/TZ, from 3.7 to 1.2 µg/ml for each component. However, prior exposure of MRSA N315 to ME/TZ (11.1 µg/ml each) or meropenem-only (33.3 µg/ml) showed a nine-fold increase in levels of resistance to ME/PI/TZ (increasing from 3.7 to 33.3 µg/ml for each component). Exposure to tazobactam-only gave intermediate gains in resistance to ME/PI/TZ up to day 7 (11.1 µg/ml each), and higher resistance at day 11 (33.3 µg/ml each). Prior exposure to ME/PI or PI/TZ generated only a threefold increase in MIC (from 3.7 to 11.1 µg/ml) over the 11 days.

Despite the elevated MICs to ME/PI/TZ in the isolates adapted to the component drugs, the triple-drug combination still maintained synergy in all adapted isolates (Table 5B). This is consistent with synergistic drug activity within the range of ME/PI/TZ MICs observed for the 72 clinical MRSA isolates (Table 4), relative to their single-drug MICs. These results show that even when genomic changes enabling sub-component resistance can be selected, the overall synergistic activity of the triple-drug combination is maintained. In contrast to recent work with a non-pathogenic E. coli strain[36], we observed no change in the overall drug interaction profile of ME/PI/TZ regarding synergy with increased resistance to any component drug.

Example 7. ME/PIT/TZ is as Effective as Linezolid Against MRSA In Vivo

Figure 5:
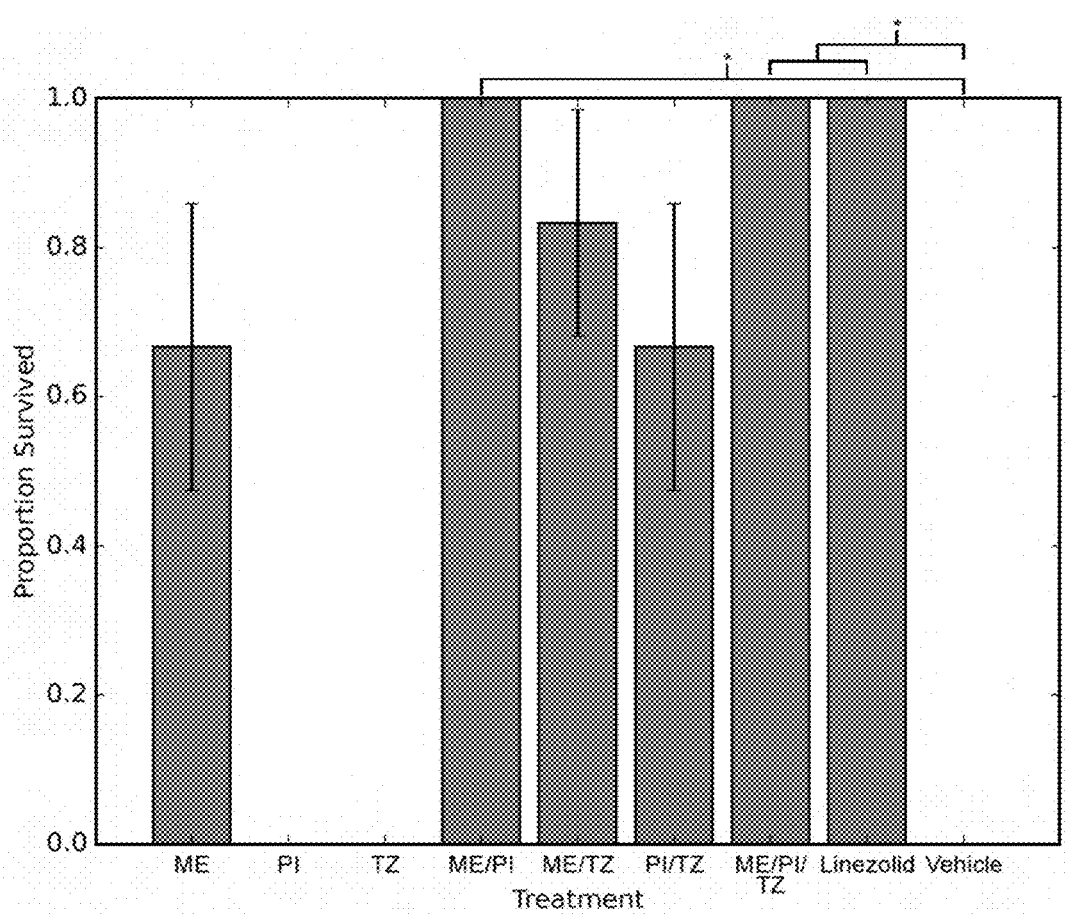
FIG. 5 depicts a graph showing efficacy of ME/PIT/TZ treatment in neutropenic mouse peritonitis model of MRSA N315. Proportional survival of mice (n=6) from each drug treatment is shown. Treatment with ME/PI/TZ, ME/PI, and linezolid are significantly different than vehicle (*p=0.02). Error bars indicate standard error of proportions of survivors per condition tested.

Next we tested if ME/PI/TZ or its constituents can be effective in treating MRSA infections in vivo using a neutropenic mouse model of peritonitis. Blood taken at 11 h post-infection from mice that were treated with either ME/PI/TZ, ME/PI (67 mg/kg each) or linezolid (30 mg/kg) yielded zero plated colonies and no growth in liquid cultures, indicating clearance of infection (FIG. 5, Table 7). All mice (n=6/group) from each of these treatments survived for six days post-infection (total duration of the mouse study). The efficacy of ME/PI/TZ and ME/PI was similar to linezolid monotherapy based on clearance of MRSA infection and survival of all treated mice compared to vehicle (p=0.02, Fisher's exact test).

In contrast to the complete rescue of the infected mice by ME/PI/TZ, ME/PI, or linezolid, several mice treated with ME/TZ, PI/TZ, or meropenem-alone, and all mice treated singly with piperacillin or tazobactam succumbed to the infection, most within 48 h (FIG. 5, Table 7). Treatment with these other drug regimens was not significantly different than treatment with vehicle (p>0.05, Fisher's exact test) (Table 6A), where all mice also succumbed to the infection within 48 h.

We tested MRSA N315 cultures from blood drawn from mice treated with meropenem, piperacillin, or vehicle for their in vitro MICs against ME/PI/TZ and its constituent single drugs to determine whether adaptation occurred during passage in vivo. All four tested isolates of MRSA N315 had identical MICs for the triple ME/PI/TZ and all constituent drugs, and thus identical synergy (Table 6B). These data suggest no adaptation occurred within these strains to overcome the triple ME/PI/TZ tested within the 11-h passage in vivo.

Discussion for the Examples

Figure 9:
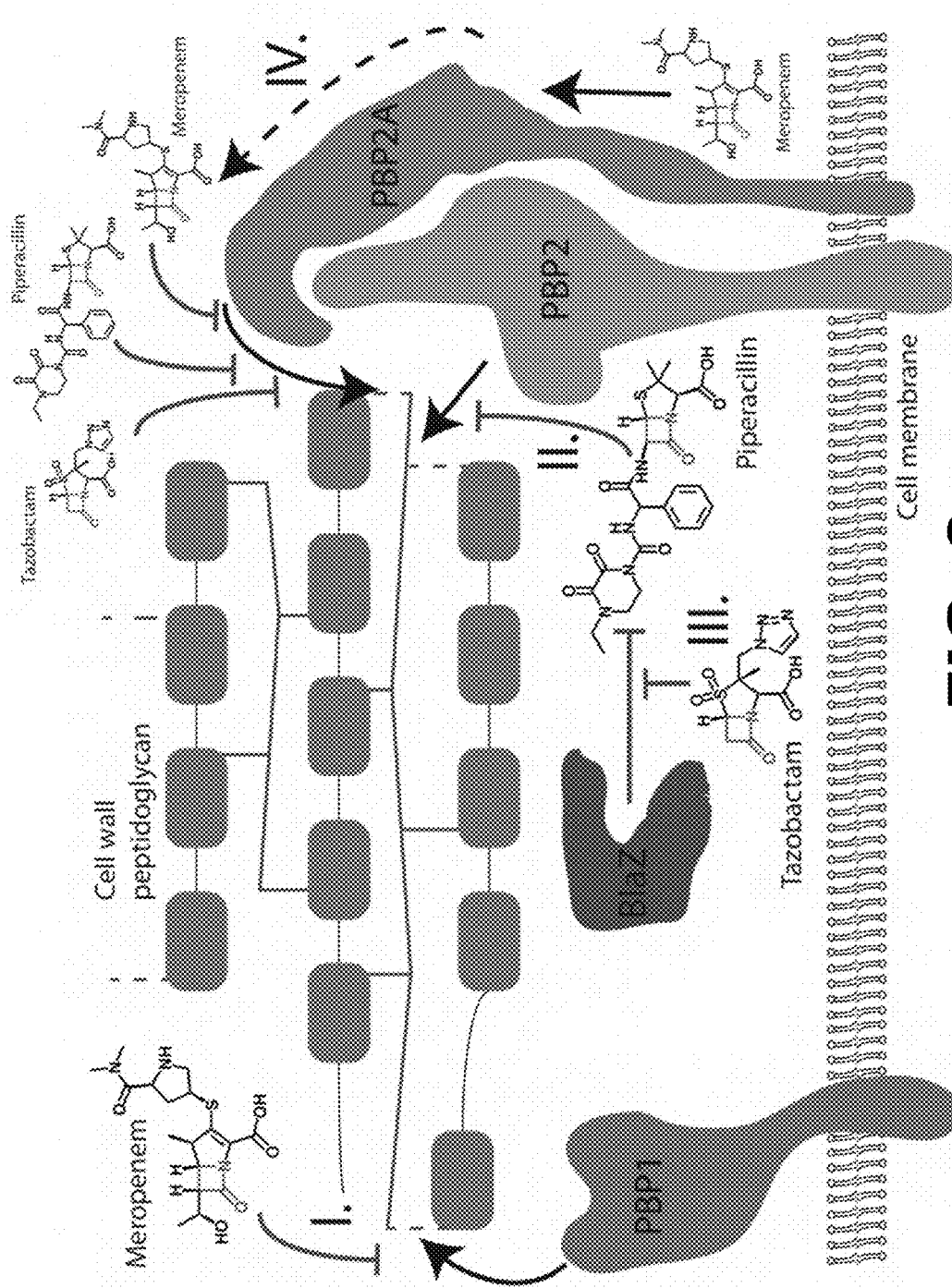
FIG. 9 depicts a proposed mechanism of synergy of meropenem/piperacillin/tazobactam (ME/PI/TZ) against MRSA. Our data support the proposed synergistic mode of action against cell-wall synthesis in MRSA involving: I.) suppression of transpeptidation by PBP1 at the division septum by carbapenems, II.) suppression of transpeptidation by PBP2 by penams (penicillins), III.) suppression of β-lactamase activity against penams by β-lactamase inhibitors, and IV.) allosteric opening of the active site of PBP2a by meropenem, allowing inhibition by meropenem or by other β-lactams.

We have shown that triple antibacterial combinations containing carbapenems, penicillins, and β-lactamase inhibitors target multiple nodes in the same cellular system (cell-wall synthesis) and are highly synergistic and bactericidal against diverse MRSA strains in vitro, at clinically achievable concentrations. This contrasts with recent work showing collateral sensitivity and synergy to arise from combinations of drug classes working against orthogonal cellular targets in non-pathogenic lab strains only[25,36]. Because carbapenems and other drugs at high concentration could have toxic effects, reduced per-drug dosages via synergy mitigate potential toxicities[55]. Our 3-D checkerboard testing confirmed the optimal input concentrations for ME/PI/TZ to be given in a 1:1:1 ratio (2 µg/ml each) against MRSA N315, which is below the susceptibility breakpoints for these compounds against methicillin-susceptible S. aureus and is an 8-to-64-fold reduction in input concentrations for these formerly inactive drugs against this highly resistant MRSA strain. Our mechanistic analyses support our hypothesis that targeting of PBP1 by meropenem, targeting of PBP2 by piperacillin, protection of piperacillin by tazobactam from β-lactamase cleavage, and allosteric opening of the active site of PBP2a by meropenem for inhibition by another molecule of antibiotic in the combination, result in synergy by simultaneously perturbing multiple components of the MRSA cell-wall synthesis system (FIG. 9).

We have also preliminarily shown that this combination has activity in a highly lethal neutropenic MRSA in vivo model, demonstrating that this triple combination of clinically approved β-lactams can clear infection similar to substantially more expensive monotherapies like linezolid. The plasma levels of meropenem observed in mice correlate well with plasma drug levels in healthy humans[56], and meropenem would attain the Kd at these clinically achievable concentrations to trigger allostery for opening of the active site of PBP2a, providing accessibility for inhibition by meropenem and other β-lactams in the combination[9,10].

Notably, the double combination ME/PI cleared the MRSA N315 infection in vivo similarly to ME/PI/TZ and linezolid within 11 h. In vitro we observed high synergy scores and reciprocal collateral sensitivity for this combination, similar to what was seen for ME/PI/TZ, but ME/PI did not suppress evolution of resistance to the same extent that ME/PI/TZ did. This property may not have been relevant to this aggressive infection model, but may be important for longer treatment times seen in human infections with MRSA. ME/PI/TZ is also likely to be effective at lower total concentrations than ME/PI because of its higher synergy. Longer exposure of the N315 strain to the tazobactam component of ME/PI/TZ in vivo may also promote ejection of pN315 plasmid with concomitant sensitization to the penicillin component, in line with the in vitro results for collateral sensitivity and suppression of adaptation. Indeed, to more adequately address this question, potential longer-term in vivo resistance evolution would need to be tested under sub-lethal concentrations of the drugs in important follow-up mouse experiments.

Our robust mechanistic in vitro results and preliminary in vivo results for ME/PI/TZ activity suggest this combination may be made immediately available for use in the clinic, since it includes currently FDA-approved drugs, which had met their obsolescence as monotherapies against MRSA decades ago. However, further mechanistic features of the combination that were shown in vitro (synergy, resistance suppression over longer periods of dosing, collateral sensitivity, etc.) will require substantially more in vivo testing to support the promising but preliminary activity observed in our highly aggressive neutropenic mouse model.

We note that high resistance to meropenem or tazobactam slightly reduces the effectiveness of ME/PI/TZ, while maintaining its synergy, and our resistance evolution analysis cannot account for resistance genes acquired horizontally that could break the relationship between meropenem, piperacillin, and tazobactam. Despite these caveats, we believe the ME/PI/TZ combination is an immediately viable anti-MRSA therapeutic, and endorse further mechanistic exploration into the putative superior efficacy of high-order antibiotic combinations that are both synergistic and encoded by collaterally sensitive constituents. Having similar activity to linezolid against MRSA in vivo, the potential efficacy of ME/PI/TZ reopens broad prospects for the clinical use of β-lactams against the staphylococci. It also suggests that this line of research into repurposing existing antibiotics in carefully designed synergistic combinations would address immediate clinical needs, as these agents are already approved for human use. Emergence of resistance to any antibiotic or any antibiotic combination is inevitable. Yet, as evidenced in our study, combinations composed of key drug-drug interaction features may be a tool in mitigating the emergence of antibiotic resistance by preserving the usefulness of existing agents available to us in our pharmacological armamentarium.

Methods for the Examples

Microbiological Studies:

MRSA N315 was a gift from Dr. Steven Gill, University of Rochester, Rochester, N.Y., USA. S. aureus ATCC 29213 was acquired from the American Type Culture Collection. De-identified clinical MRSA isolates were selected at random from the clinical isolate strain bank at Barnes-Jewish Hospital, St. Louis, Mo., USA. Minimal inhibitory concentration (MIC) assays for inhibition of growth were performed following the recommendations of the Clinical and Laboratory Standards Institute (CLSI)[43]. Briefly, 23 antibacterial compounds (Supplemental Table 1) were selected based on coverage of all major drug classes, including three compounds not classified as antibiotics for human use, but with known antibacterial properties. Compounds were dissolved in dimethyl sulfoxide (DMSO) to a stock concentration of 50 mg/ml. Exceptions: Sulfometuron at 20 mg/ml in DMSO; Tobramycin, D-cycloserine, and colistin at 50 mg/ml in $H_2O$ and filtered at 2 μm. The 23 compounds were formulated into all 253 possible unique pairwise combinations at fixed ratios and at 100× concentrations in solvent. To increase the range of concentrations assayed for possible synergistic or antagonistic drug interactions (>2,000-fold), the drug stocks were arrayed into threefold dilution series down eight rows in 96-well Costar master drug plates, using a BioMek FX robotic liquid handler (Beckman Coulter, Inc.). Drugs were then mixed 1:100 into 96-well plates containing 200 μl/well of cation-adjusted Mueller-Hinton broth (CAMHB). All drug susceptibility assay wells were inoculated with ~1 μl of mid-log phase bacterial culture at 0.5 McFarland standard (~2×10$^8$ CFU/ml) and grown at 37° C. for 24 h. Endpoint growth at 37° C. after 24 h was determined by optical density at 600 nm≥0.1 using a Synergy H1 reader (BioTek, Inc.).

Synergy of antibiotic combinations was determined using the fractional inhibitory concentration index (FICI) method[57,58]. By this method, the MIC of the antibiotic compound in combination is divided by the MIC of the compound alone, yielding the fractional contribution of each drug component in the combination. Quotients for all in a combination are summed and drug interactions scored using the formula: $FICI=(MIC\ A_{comb\ A\ B\ C})/MIC_{agent\ A}+(MIC\ B_{comb\ A\ B\ C})/MIC_{agent\ B}+(MIC\ C_{comb\ A\ B\ C})/MIC_{agentC}$ Select pairwise combinations against MRSA were then combined with each of the 21 remaining single drugs to make triple combinations, formulated and tested in identical fashion to the double combinations. Synergy of combinations was confirmed via triplicate measurements of drug conditions at the MIC. Based on its high synergy against MRSA N315 in the sparse screening, ME/PI/TZ and its constituents were selected for further characterization. Final susceptibility testing of ME/PI/TZ and its components was performed using twofold dilution from 128 to 2 μg/ml for each component Minimal bactericidal concentration (MBC) for ME/PI/TZ in MRSA N315 was determined via duplicate wells of ME/PI/TZ at indicated concentrations in CAMHB media, inoculated with ~5×10$^5$ CFU/ml of MRSA N315 in mid-log phase and incubated at 37° C. for 24 h. 100 μl of a 1:100 dilution of 50 μl drawn from duplicate ME/PI/TZ wells was plated on Mueller-Hinton agar (MHA) plates and incubated overnight for 24 h. No colony growth at or two dilutions above the MIC confirmed bactericidal activity, as defined by CLSI[59]. Meropenem (CAS 96036-03-2) and clavulanate (CAS 61177-45-5) were obtained from AK Scientific, Inc. (Union City, Calif., USA). Piperacillin (CAS 59703-84-3), tazobactam (CAS 89786-04-9), imipenem (CAS 74431-23-5), and amoxicillin (CAS 26787-78-0) were obtained from Sigma-Aldrich Co. (St. Louis, Mo., USA).

Adaptation and Cross-Resistance Assays:

414 MRSA N315 was grown in 150 μl/well of CAMHB with constant shaking at 37° C. and passaged over 11 days in identical 96-well plates containing replicate threefold dilutions of ME/PI/TZ, ME/PI, ME/TZ, PI/TZ, ME, PI, and TZ. Top concentrations of drug combinations were 33.3 μg/ml for each component, while top concentrations for single drugs was 100 μg/ml. To test for cell viability, at the end of the assay on day 11, all wells from the plate were pinned with a sterile 96-pin replicator and transferred to CAMHB only. After passage, plates were filled 1:1 with 30% CAMHB/glycerol and frozen at −80° C. for later analysis.

Growth rate of isolates over passages in each condition was determined by linear best-fit of logarithm-converted exponential growth phase. Following Hegreness et al[23], those wells containing cells in drug conditions whose growth rates were >0.2 h$^{-1}$ between day one and the average of the last six days of growth were considered significantly adapting to conditions and an adaptation rate α was generated. Adapted isolates were retrospectively chosen from each combination or single compound in wells showing an increase in MIC or growth rate, frozen isolates were streaked out on agar plates to obtain single colonies, re-grown in broth conditions identical to those in which they grew originally, and then re-inoculated in sterile 96-well plates identical to the original 11-day 431 plates.

Expression Profiling with qRT-PCR:

Wild-type and adapted MRSA N315 isolates were grown in triplicate in 100 ml flasks to mid-log phase in CAMHB+/− piperacillin at 11.1 µg/ml or tazobactam at 33.3 µg/ml. To harvest cells at mid-log phase, each culture flask was split into 2×50 ml screw-cap tubes, spun down at 4° C. for 10 min at 3500 rpm, supernatant removed, and pellets combined carefully with a 2 ml serological pipette. 1 ml RNAprotect Bacteria Reagent (Qiagen, Valencia, Calif., USA) was added to pellets to stabilize the RNA, vortexed briefly, and incubated for 5 min at RT. After incubation, tubes were spun again at 4° C. for 10 min at 3500 rpm, supernatant removed, and the pellets were stored at −80° C. Total RNA was extracted by the following protocol:

(1) Resuspend cell pellets in 500 µl Buffer B (200 mM NaCl, 20 mM EDTA).
(2) Add 210 µl 20% SDS.
(3) Add ~250 µl volume of acid-washed sterile glass beads (Sigma, Inc.).
(4) Add 500 µl Phenol:Chloroform:IAA.
(5) Bead beat on 'high' for 5 min.
(6) Spin at 8000 rpm at 4° C. for 3 min (to separate the phases).
(7) Remove top aqueous phase and transfer into a new tube.
(8) Add 700 µl isopropanol.
(9) Add 70 µl 3M NaOAc, mix thoroughly by inversion.
(10) Spin at 4° C., max rpm, for 10 min.
(11) Aspirate supernatant.
(12) Add 750 µl ice cold 70% EtOH, spin at max rpm at 4° C. for 5 min.
(13) Aspirate supernatant, to let the EtOH dry, leave tubes open in RNase free area.
(14) Add 100 µl nuclease free water to each tube and resuspend (put tubes in 50° C. heat block, vortexing periodically).
(15) Add 12 µl TURBO-DNase buffer (Ambion, Inc.) and 10 µl RNase-free TURBO-DNase to each sample, and incubate at 37° C. for 30 min.
(16) Purify samples using MEGAClear columns and kit per manufacturer protocol.
(17) Re-purify samples using Baseline-ZERO DNase buffer (Epicentre, Inc.) and 10 µl Baseline-ZERO DNase, following manufacturer protocol.
(18) Elute final RNA samples with 30 µl TE buffer, pH 7.0.

First-strand cDNA was synthesized from total RNA with SuperScript First-Strand Synthesis System for RT-PCR (Life Technologies, Carlsbad, Calif., USA). qRT-PCR of pbp2, mecA and blaZ in MRSA N315 was performed against gyrB using SYBR Select Master Mix for CFX (Life Technologies, Carlsbad, Calif., USA) on a CFX96 Real-Time PCR Detection System (Bio-Rad Laboratories, Inc, Hercules, Calif., USA). Primer sequences used (0.3 µM each):

pbp2_F: SEQ ID NO: 1
CGTGCCGAAATCAATGAAAGACGC, pbp2_R: SEQ ID NO: 2
GGCACCTTCAGAACCAAATCCACC;

mecA_F: SEQ ID NO: 3
TGGAACGATGCCTATCTCATATGC, mecA_R: SEQ ID NO: 4
CAGGAATGCAGAAAGACCAAAGC;

blaZ_F: SEQ ID NO: 5
TTTATCAGCAACCTTATAGTCTTTTGGAAC, blaZ_R: SEQ ID NO: 6
CCTGCTGCTTTCGGCAAGAC, gyrB_F: SEQ ID NO: 7
CGATGTGGATGGAGCGCATATTAG, gyrB_R: SEQ ID NO: 8
ACAACGGTGGCTGTGCAATATAC.

CFX protocol: 2 min @ 50° C., 2 min @ 95° C., (15 s @ 95° C., 1 min @ 60° C.)×40 cycles. Gene expression was determined using the ΔΔCt method of normalized quantitation 60, where Ct indicates the cycle number at which exponential growth phase increases above threshold fluorescence signal.

Sequencing Library Preparation:

Genomic DNA (gDNA) was extracted from wild-type and adapted MRSA N315 using lysostaphin digestion and phenol:chloroform:IAA extraction as follows:

(1) Draw 1 ml aliquots from overnight 5 ml shaking cultures of S. aureus strains, spin down at 13,000 rpm for 3 min, pour off media, add additional 1 ml of culture and repeat.
(2) Add 500 µl of 2× Buffer A (NaCl 200 mM, Tris 200 mM, EDTA 20 mM) at 4° C. to pelleted cells and vortex briefly to resuspend cells.
(3) Add 2.5 µl of 10 mg/ml (200λ) lysostaphin (Sigma-Aldrich, Inc.) to tubes.
(4) Flick mix and spin down tubes, place in 37° C. dry bath for 1 h.
(5) Fast cool micro-centrifuge to 4° C.
(6) Add ~250 µl of 0.1 mm zirconium beads (BioSpec Products, cat#1107910).
(7) Add 210 µl of 20% SDS.
(8) Add 500 µl phenol:chloroform:IAA (25:24:1, pH 7.9), chill samples on ice.
(9) Bead beat on the "homogenize" setting for 4 min (beat 2 min, ice 2 min, beat 2 min).
(10) Spin at 6800 rcf (4° C.) for 3 min.
(11) Spin down PLG columns (5Prime, cat#2302820) at max speed (20,800 rcf) for 30 s at RT while waiting.
(12) Transfer aqueous phase (~500 µl) to pre-spun phase-lock gel tube.
(13) Add equal amount (500 µl) of phenol:chloroform:IAA (25:24:1, pH 7.9) to tube and mix by inversion (DO NOT VORTEX).
(14) Spin tubes at max speed (20,800 rcf) (RT) for 5 min.
(15) Transfer aqueous phase (~500 µl) to a new Eppendorf tube.
(16) Add 500 µl of −20° C. isopropanol.
(17) Add 50 µl (1/10 vol.) of 3M NaOAc at pH 5.5 (Ambion, AM9740), and mix thoroughly by inversion.
(18) Store at −20° C. for at least 1 h (overnight is preferable but not necessary).
(19) Spin at max speed at 4° C. for 20 min.
(20) Wash pellet with 500 µl of 100% EtOH (RT) and spin down at 4° C. for 3 min.

(21) Carefully pipet off EtOH, air-dry >15 min.
(22) Add 30 µl of TE (Ambion, AM 9861), incubate at 50° C. for 5 min.
(23) Run DNA through QIAGEN QIAQuick PCR purification column with the following modifications: RNase A treatment at beginning of column clean-up. Combine 4 µl Qiagen RNase (100 mg/ml) with every 300 µl buffer PB used, incubate in buffer PB/RNase for 15 min at RT.
(24) Let PE wash buffer sit in column at RT for 2 min, elute gDNA with 35 µl of EB buffer pre-heated to 55° C., letting sit for 1 min before final spin.

We sheared 500 ng of total DNA from each genome to ~300 bp fragments in nine rounds of shearing of ten min each on the BioRuptor XL. In each round the power setting was CH' and samples were treated for 30 s and allowed to rest for 30 s. Each sample was concentrated using the Qiagen MinElute PCR purification kit per the manufacturer's protocol. End Repair of the sheared DNA fragments was initiated with the addition of 2.5 µl of T4 DNA ligase buffer with 10 mM ATP (NEB, B0202S), 1 µl of 1 mM dNTPs (NEB), 0.5 µl T4 Polymerase (NEB, M0203S), 0.5 µl T4 PNK (NEB M0201S), and 0.5 µl Taq Polymerase (NEB, M0267S). This mixture was incubated at 25° C. for 30 min, then at 75° C. for 20 min. Barcoded adapters were then added to the solution along with 0.8 µl of T4 DNA ligase (NEB, M0202M), for the purpose of ligating the adapters to the DNA fragments. This solution was then incubated at 16° C. for 40 min, then 65° C. for 10 min. The adapter-ligated DNA was then purified using the Qiagen MinElute PCR purification kit per the manufacturer's protocol.

The DNA fragments were then size selected on a 2% agarose gel in 1×TBE buffer stained with Biotium GelGreen dye (Biotium). DNA fragments were combined with 2.5 µl 6× Orange loading dye before loading on to the gel. Adapter-ligated DNA was extracted from gel slices corresponding to DNA of 250-300 bp using a QIAGEN MinElute Gel Extraction kit per the manufacturer's protocol. The purified DNA was enriched by PCR using 12.5 µl 2× Phusion HF Master Mix and 1 µl of 10 µM Illumina PCR Primer Mix in a 25 µl reaction using 1 µl of purified DNA as template. DNA was amplified at 98° C. for 30 s followed by 18 cycles of 98° C. for 10 s, 65° C. for 30 s, 72° C. for 30 s with a final extension of 5 min at 72° C. The DNA concentration was then measured using the Qubit fluorometer and 10 nmol of each sample (up to 106 samples per lane of sequencing) were pooled. Subsequently, samples were submitted for Illumina HiSeq-2500 Paired-End (PE) 101 bp sequencing at GTAC (Genome Technology Access Center, Washington University in St. Louis) at 9 pmol per lane.

DNA Sequence Analysis:

Alignment and variant calling. For the wild-type and adapted MRSA N315, all sequencing reads for each genome were de-multiplexed by barcode into separate genome bins. Reads were quality trimmed to remove adapter sequence and bases on either end with a quality score below 19. Any reads shorter than 31 bp after quality trimming were not used in further analysis. All reads were mapped to the *Staphylococcus aureus* subsp. *aureus* N315 chromosome (GenBank ID: BA000018.3) and pN315 plasmid (GenBank ID: AP003139) (command: bowtie2-x<reference_genome_index_name>-1<forward_read_file>-2 <reverse_read_file>-q—phred33—very-sensitive-local-I 200-X 1000-S <sam_output>). Variants from the reference were called using samtools[61] commands: samtools view-buS <sam_file>|samtools sort-m 4000000000-<sample_prefix>### samtools index <bam_file>### samtools mpileup-uD-f reference_genome><bam_file>|bcftools view-bcv-> <bcf_file>### bcftools view <bcf_file>). The variant call format (VCF) file was then filtered to remove SNPs with a quality score lower than 70 or coverage greater than twice the average coverage expected per base. Absence of read coverage or overabundant read coverage indicated plasmid loss or large duplication respectively. Any variant position found from the wild-type alignment was determined to be a result of alignment error or to be derived from lab specific drift in N315 and was removed from all other VCF files. Each variant position was then compared to known ORF locations in N315 to search for causal variants.

In Vivo Mouse Model of MRSA Infection:

Animals. Outbred ICR female mice (6-8 weeks old, 17-25 g body weight; Harlan Laboratories, Inc., Indianapolis, Ind., USA) were used. Mice were given Teklad 2019 Extruded Rodent Diet (Harlan Laboratories, Inc., Indianapolis, Ind., USA) and water ad libitum. Mice were maintained in polycarbonate shoebox cages containing corncob (The Andersons, Inc., Maumee, Ohio, USA) and Alpha-dri (Shepherd Specialty Papers, Inc., Richland, Mich., USA) bedding under 12-h light/12-h dark cycle at 22±1° C. All procedures involving animals were approved by the University of Notre Dame Institutional Animal Care and Use Committee.

Neutropenic Mouse Peritonitis Model of MRSA Infection.

Doses of cyclophosphamide (100 µl of 50 mg/ml in 0.9% saline corresponding to 200 mg/kg; Alfa Aesar, Ward Hill, Mass., USA) were given intraperitoneally (IP) at 4 days and 1 day prior to infection. The S. strain N315 was streaked onto Brain-Heart Infusion (BHI; Becton Dickson and Company, Sparks, Md., USA) agar and grown overnight at 36° C. The MRSA N315 bacterial inoculum was adjusted to approximately $1 \times 10^8$ CFU/ml (corresponding to $OD_{540}$=0.5), then diluted to give $2 \times 10^7$ CFU/ml. A 10% porcine mucin (Sigma-Aldrich, St. Louis, Mo., USA) suspension was prepared and adjusted to pH 7. Immediately prior to infection, the bacterial inocula were diluted 1:1 with 10% mucin to a final concentration of $1 \times 10^7$ CFU/ml in 5% mucin. The mice were then infected IP with 0.5 ml of this inoculum. In vivo dosing of compounds in mice was compared with mean or range peak human plasma concentrations of studied β-lactams[44,46,47,62,63].

Antibiotic Preparation.

Meropenem was obtained from AK Scientific, Inc. (Union City, Calif., USA), piperacillin and tazobactam were obtained from Sigma-Aldrich Co. (St. Louis, Mo., USA). Linezolid (CAS 165800-03-3) was obtained from AmplaChem (Carmel, Ind., USA). Antibiotics were dissolved at a concentration of 16.67 mg/ml in 30% DMSO/30% propylene glycol/40% water. Linezolid was used as positive control and was prepared at 7.5 mg/ml. Vehicle (30% DMSO/30% propylene glycol/40% water) was included as negative control. The dosing formulations were sterilized by passing through 0.2 µm filter prior to injection.

Bacterial Isolation from Blood.

Blood samples were checked for bacterial growth by plating and liquid culture. Whole blood (100 µl, three samples per group) was spread onto Brain-Heart Infusion (BHI) agar plates and incubated at 36° C. overnight. Colonies were counted and three colonies were selected, grown overnight in liquid BHI culture at 36° C., then mixed 1:1 with 30% LB-glycerol and stored at −80° C. The remaining three blood samples of each group (50 µl) was added to 5 ml BHI broth and incubated overnight at 36° C. When growth was noted, cultures were mixed 1:1 with 30% LB-glycerol and stored at −80° C.

Statistical Analyses:

Data for minimal inhibitory concentrations (MICs) are derived from triplicate measurements. Adaptation data are taken from two replicate experiments for each drug combination condition. Data for qRT-PCR expression profiling are derived from three replicate experiments taken from three biological replicates each, with standard error of measurement calculated. Mice were treated in groups of six, and growth determination of bacteria determined via plate and broth culture in triplicate. Fisher's Exact test with Bonferroni correction was used for 8 independent tests (comparing each treatment to 610 vehicle).

TABLE 1

23 antibacterial compounds used to formulate combinations in this study.

| Compound | Target mechanism in bacteria | Antibiotic Class | MIC in MRSA N315 (µg/ml) |
|---|---|---|---|
| Sulfamethoxazole | Folic acid pathway | Sulfonamide | 100 |
| Trimethoprim | Folic acid pathway | Pyrimidine derivative | 6.2 |
| Levofloxacin | DNA synthesis | Fluoroquinolone | 0.4 |
| Bleomycin | DNA synthesis | Glycopeptide | >500 |
| Gemfibrozil | Lipid synthesis | *Fibrate (hyperlipidemia agent) | >200 |
| Sulfometuron | Amino acid biosynthesis | *Broad-spectrum urea herbicide | >200 |
| Disulfiram | Osmotic stress response | *Thiuram disulfide (anti-alcohol therapeutic) | 11.1 |
| Tigecycline | Protein synthesis | Tetracycline | 0.4 |
| Mupirocin | Protein synthesis | Pseudomonic acid | 0.4 |
| Linezolid | Protein synthesis | Oxazolidinone | 3.7 |
| Azithromycin | Protein synthesis | Macrolide | >200 |
| Clindamycin | Protein synthesis | Lincosamide | >500 |
| Chloramphenicol | Protein synthesis | Amphenicol | 11.1 |
| Tobramycin | Protein synthesis | Aminoglycoside | >500 |
| Rifampin | Transcription | Rifamycin | 0.4 |
| Vancomycin | Cell wall synthesis | Glycopeptide | 0.4 |
| Piperacillin | Cell wall synthesis | β-lactam/Penicillin (Penam)/Broad-spectrum | 64 |
| Aztreonam | Cell wall synthesis | β-lactam/Monobactam/Gram-negative specific | >500 |
| Cefepime | Cell wall synthesis | β-lactam/Cephalosporin 4$^{th}$ generation (Cephem)/Broad-spectrum | 100 |
| Meropenem | Cell wall synthesis | β-lactam/Carbapenem/Ultra-broad-spectrum | 16 |
| Tazobactam | Cell wall synthesis | β-lactamase inhibitor (Penam) | 128 |
| D-Cycloserine | Cell wall synthesis | Analogue of the amino acid D-alanine | 56 |
| Colistin | Cell membrane lysis | Polymyxin | 500 |

Compounds are grouped by target mechanism of action.
*Compound not formally classified as an antibiotic drug, but has known antibacterial properties.

TABLE 2

Fractional Inhibitory Concentration Index (FICI) profiling of combinations.

A. Interpretive criteria for FICI scoring.

| FICI | Interpretation |
|---|---|
| ≤0.5 | Synergy |
| >0.5 to <1.0 | Partial Synergy |
| 1.0 | Additivity |
| >1.0 to <4.0 | Indifference |
| ≥4.0 | Antagonism |

| Combination in stream | ME/ PI/ TZ | CP/ PI/ TZ | AZ/ PI/ TZ | ME/ AX/ TZ | ME/ AX/ CV | IM/ PI/ CV | ME/PI | ME/TZ | PI/TZ | IM/PI | IM/CV | PI/CV |
|---|---|---|---|---|---|---|---|---|---|---|---|---|
| B. FICI profiles of various triple combinations of carbapenems/penicillins/β-lactamase inhibitors against MRSA and MSSA strains. |||||||||||||
| MRSA N315 SCCmec type II | 0.11 | 0.33 | 0.33 | 0.04 | 0.41 | 0.06 | 0.44 | 0.67 | 0.22 | 0.15 | 0.67 | 0.44 |
| MRSA #181 SCCmec type II | 0.28 | ND | ND | 0.55 | ND | 0.11 | ND | ND | ND | ND | ND | ND |
| MSSA ATCC 29213 | 1.12 | ND | ND | ND | ND | 1.14 | 2.97 | 8.61 | 0.36 | 1.11 | 1.04 | 0.43 |
| C. MIC profiles of same combinations (µg/ml) Constituent double combinations are shown for comparison. |||||||||||||
| MRSA N315 SCCmec type II | 2 each | 11.1 each | 11.1 each | 0.4 each | 3.7 each | 0.12/ 1.2/ 1.2 | 2/4 | 8/2 | 16/2 | 0.37/ 3.7 | 1.11/ 1.11 | 1.11 each |
| MRSA #181 SCCmec type II | 11.1 each | ND | ND | 11.1 each | ND | 0.37/ 3.7/ 3.7 | ND | ND | ND | ND | ND | ND |

TABLE 2-continued

Fractional Inhibitory Concentration Index (FICI) profiling of combinations.

| MSSA ATCC 29213 | 0.27 each | ND | ND | ND | ND | 0.04/ 0.4/ 0.4 | 0.4 each | 1.2 each | 1.2 each | 0.04/ 0.4 | 0.04/ 0.4 | 1.2 each |
|---|---|---|---|---|---|---|---|---|---|---|---|---|

TABLE 3

Compiled FICI data for ME/PI/TZ against MRSA N315 and 72 clinical MRSA isolates.
A-B. 72 clinical BRSA isolates (with SCCmec type, if known) and FICI scores for ME/PI/TZ against 72 clinical MRSA isolates.

| A | | B | |
|---|---|---|---|
| Clinical MRSA isolate (SCCmec type) | FICI score | Clinical MRSA isolate (SCCmec type) (Continued) | FICI score (Continued) |
| 4 | 0.22 | 124 | 0.28 |
| 7 | 0.22 | 131 (II) | 0.37 |
| 13 | 0.15 | 132 | 0.22 |
| 15 | 0.5 | 140 | 0.22 |
| 22 | 0.22 | 144 | 0.15 |
| 25 | 0.22 | 146 | 0.22 |
| 27 | 0.67 | 150 | 0.67 |
| 31 | 0.15 | 152 | 0.22 |
| 35 (II) | 0.17 | 155 | 0.39 |
| 37 | 0.15 | 161 | 0.37 |
| 39 (II) | 0.67 | 163 | 0.37 |
| 41 (II) | 0.09 | 164 | 0.17 |
| 45 | 0.22 | 165 | 0.15 |
| 48 | 0.15 | 167 | 0.22 |
| 53 | 0.22 | 168 | 0.22 |
| 59 | 0.07 | 169 | 0.17 |
| 64 (II) | 0.44 | 171 | 0.17 |
| 66 | 0.11 | 172 | 0.67 |
| 70 | 0.67 | 175 | 0.15 |
| 72 | 0.15 | 177 | 0.22 |
| 73 (IV) | 0.34 | 181 (II) | 0.28 |
| 74 | 0.34 | 182 | 0.5 |
| 75 | 0.34 | 189 | 0.15 |
| 77 (II) | 0.67 | 190 | 0.34 |
| 85 | 0.5 | 193 (II) | 0.34 |
| 89 | 0.07 | 194 | 0.15 |
| 90 | 0.22 | 195 | 0.15 |
| 95 | 0.22 | 197 | 0.15 |
| 99 | 0.44 | 200 | 0.15 |
| 101 | 0.22 | 201 | 0.44 |
| 103 | 0.37 | 204 | 0.39 |
| 104 (II) | 0.15 | 205 | 0.22 |
| 109 | 0.17 | 206 | 0.22 |
| 118 | 0.07 | 213 | 0.44 |
| 121 | 0.22 | 217 | 0.15 |
| 122 | 0.22 | 219 | 0.15 |

TABLE 4

Compiled MIC and MBC data for ME/PI/TZ against MRSA isolates.

A. Distribution of MIC resistance profiles of studied MRSA isolates against ME/PI/TZ.

| MIC of ME/PI/TZ Components (µg/ml) | # of MRSA isolates | % of total |
|---|---|---|
| 33.3 | 9 | 12.3 |
| 11.1 | 27 | 36.9 |
| 3.7 | 27 | 36.9 |
| 1.2 | 8 | 10.9 |
| 0.4 | 2 | 2.7 |
| Total | 73 | — |

B. Confirmation of minimum bactericidal concentration (MBC) for ME/PI/TZ in MRSA N315.

| Plate Concentrations | Colonies Plate A | Colonies Plate B |
|---|---|---|
| ME/PI/TZ 2/2/2 | Punctate lawn | Too many to count |
| ME/PI/TZ 4/4/4* | 40 | 0 |
| ME/PI/TZ 8/8/8 | 2 | 0 |
| ME/PI/TZ 16/16/16 | 0 | 0 |
| ME/PI/TZ 32/32/32 | 8 | 0 |

*MIC = 4/4/4 µg/ml

TABLE 5

Change in ME/PI/TZ resistance phenotype of MRSA N315 over 11 days after repeated exposure to constituents of ME/PI/TZ.

A. Isolates were selected on days when an increase in MIC or growth rate was noted. Antibacterial concentrations (listed in µg/ml) show the adaptation conditions for MRSA N315. Post-adaptation MICs to each component of ME/PI/TZ are shown in selected isolates versus passage day.

| Passage day/ Adaptation conditions | ME/PI 11.1 µg/ml each | ME/TZ 11.1 µg/ml each | PI/TZ 3.7 µg/ml each | Meropenem 33.3 µg/ml | Piperacillin 100 µg/ml | Piperacillin 33.3 µg/ml | Tazobactam 100 µg/ml |
|---|---|---|---|---|---|---|---|
| 1 | no change | 11.1/11.1/ 11.1 | 1.2/1.2/1.2 | 11.1/11.1/ 11.1 | no change | 1.2/1.2/1.2 | 11.1/11.1/ 11.1 |
| 2 | no change | no change | no change | no change | 3.7/3.7/3.7 | 3.7/3.7/3.7 | 11.1/11.1/ 11.1 |
| 3 | no change | no change | no change | no change | no change | no change | no change |
| 4 | no change | no change | no change | no change | no change | no change | no change |

TABLE 5-continued

Change in ME/PI/TZ resistance phenotype of MRSA N315 over 11 days after repeated exposure to constituents of ME/PI/TZ.

| | | | | | | | |
|---|---|---|---|---|---|---|---|
| 5 | no change | 33.3/33.3/33.3 | no change | no change | no change | no change | no change |
| 6 | no change | no change | 11.1/11.1/11.1 | no change | no change | no change | no change |
| 7 | 11.1/11.1/11.1 | no change | no change | 33.3/33.3/33.3 | no change | no change | 11.1/11.1/11.1 |
| 8 | no change | no change | no change | no change | 1.2/1.2/1.2 | 1.2/1.2/1.2 | no change |
| 9 | no change | no change | no change | no change | no change | no change | no change |
| 10 | no change | no change | no change | no change | no change | no change | no change |
| 11 | 11.1/11.1/11.1 | 33.3/33.3/33.3 | 11.1/11.1/11.1 | 33.3/33.3/33.3 | 1.2/1.2/1.2 | 1.2/1.2/1.2 | 33.3/33.3/33.3 |

B. FICI of MRSA N315 against ME/PI/TZ after adaptation components in vitro.

| MRSA N315 isolate adapted to: | ME/PI | ME/TZ | PI/TZ | ME | PI | TZ |
|---|---|---|---|---|---|---|
| FICI ME/PI/TZ | 0.22 | 0.83 | 0.22 | 0.83 | 0.05 | 0.83 |

TABLE 6

A. Statistics of in vivo treatments with β-lactams

| Drug condition tested | p-value versus vehicle | After multiple hypothesis correction (Bonferroni) |
|---|---|---|
| ME | 0.6006 | 4.848 (1) |
| PI | 1 | 8 (1) |
| TZ | 1 | 8 (1) |
| ME/PI | 0.0022 | 0.0176 |
| ME/TZ | 0.0152 | 0.1216 |
| PI/TZ | 0.606 | 4.848 (1) |
| ME/PI/TZ | 0.0022 | 0.0176 |
| Linezolid | 0.0022 | 0.0176 |

B. In vitro MICs and FICI scores for MRSA N315 after passage in vivo under indicated drug conditions.

| Colonies from mice given: MIC (µg/ml) for: | ME | PI | Vehicle | Wild-type N315 |
|---|---|---|---|---|
| ME/PI/TZ | 3.7/3.7/3.7 | 3.7/3.7/3.7 | 3.7/3.7/3.7 | 3.7/3.7/3.7 |
| ME | 33.3 | 33.3 | 33.3 | 33.3 |
| PI | 33.3 | 33.3 | 33.3 | 33.3 |
| TZ | 100 | 100 | 100 | 100 |
| FICI | 0.26 | 0.26 | 0.26 | 0.26 |

TABLE 7

Data from Animal Experiments

| MRSA ID | Time of Inf | Compound (Dose level) | dose every 8 hrs SC | 2nd dose SC | Cheek Bleed | 3rd dose SC |
|---|---|---|---|---|---|---|
| 1 | 7:30 AM | meropenem (67 mg/kg) | 8:30 AM | 4:30 PM | 6:31 PM | 12:31 AM |
| 2 | 7:31 AM | meropenem (67 mg/kg) | 8:31 AM | 4:31 PM | 6:32 PM | 12:32 AM |
| 3 | 7:32 AM | meropenem (67 mg/kg) | 8:32 AM | 4:32 PM | 6:33 PM | 12:33 AM |
| 4 | 7:33 AM | meropenem (67 mg/kg) | 8:33 AM | 4:33 PM | 6:34 PM | 12:34 AM |
| 5 | 7:34 AM | meropenem (67 mg/kg) | 8:34 AM | 4:34 PM | 6:35 PM | 12:35 AM |
| 6 | 7:35 AM | meropenem (67 mg/kg) | 8:35 AM | 4:35 PM | 6:36 PM | 12:36 AM |
| 7 | 7:40 AM | piperacillin (67 mg/kg) | 8:40 AM | 4:40 PM | 6:41 PM | 12:41 AM |
| 8 | 7:41 AM | piperacillin (67 mg/kg) | 8:41 AM | 4:41 PM | 6:42 PM | 12:42 AM |
| 9 | 7:42 AM | piperacillin (67 mg/kg) | 8:42 AM | 4:42 PM | 6:43 PM | 12:43 AM |
| 10 | 7:43 AM | piperacillin (67 mg/kg) | 8:43 AM | 4:43 PM | 6:44 PM | 12:44 AM |
| 11 | 7:44 AM | piperacillin (67 mg/kg) | 8:44 AM | 4:44 PM | 6:45 PM | 12:45 AM |
| 12 | 7:45 AM | piperacillin (67 mg/kg) | 8:45 AM | 4:45 PM | 6:46 PM | 12:46 AM |
| 13 | 7:50 AM | tazobactam (67 mg/kg) | 8:50 AM | 4:50 PM | 6:51 PM | 12:51 AM |
| 14 | 7:51 AM | tazobactam (67 mg/kg) | 8:51 AM | 4:51 PM | 6:52 PM | 12:52 AM |
| 15 | 7:52 AM | tazobactam (67 mg/kg) | 8:52 AM | 4:52 PM | 6:53 PM | 12:53 AM |
| 16 | 7:53 AM | tazobactam (67 mg/kg) | 8:53 AM | 4:53 PM | 6:54 PM | 12:54 AM |
| 17 | 7:54 AM | tazobactam (67 mg/kg) | 8:54 AM | 4:54 PM | 6:55 PM | 12:55 AM |
| 18 | 7:55 AM | tazobactam (67 mg/kg) | 8:55 AM | 4:55 PM | 6:56 PM | 12:56 AM |
| 19 | 8:00 AM | meropenem + piperacillin (67 mg/kg of each) | 9:00 AM | 5:00 PM | 7:01 PM | 1:01 AM |
| 20 | 8:01 AM | meropenem + piperacillin (67 mg/kg of each) | 9:01 AM | 5:01 PM | 7:02 PM | 1:02 AM |
| 21 | 8:02 AM | meropenem + piperacillin (67 mg/kg of each) | 9:02 AM | 5:02 PM | 7:03 PM | 1:03 AM |
| 22 | 8:03 AM | meropenem + piperacillin (67 mg/kg of each) | 9:03 AM | 5:03 PM | 7:04 PM | 1:04 AM |
| 23 | 8:04 AM | meropenem + piperacillin (67 mg/kg of each) | 9:04 AM | 5:04 PM | 7:05 PM | 1:05 AM |

TABLE 7-continued

Data from Animal Experiments

| ID | | | | | | |
|---|---|---|---|---|---|---|
| 24 | 8:05 AM | meropenem + piperacillin (67 mg/kg of each) | 9:05 AM | 5:05 PM | 7:06 PM | 1:06 AM |
| 25 | 8:10 AM | meropenem + tazobactam (67 mg/kg of each) | 9:10 AM | 5:10 PM | 7:11 PM | 1:11 AM |
| 26 | 8:11 AM | meropenem + tazobactam (67 mg/kg of each) | 9:11 AM | 5:11 PM | 7:12 PM | 1:12 AM |
| 27 | 8:12 AM | meropenem + tazobactam (67 mg/kg of each) | 9:12 AM | 5:12 PM | 7:13 PM | 1:13 AM |
| 28 | 8:13 AM | meropenem + tazobactam (67 mg/kg of each) | 9:13 AM | 5:13 PM | 7:14 PM | 1:14 AM |
| 29 | 8:14 AM | meropenem + tazobactam (67 mg/kg of each) | 9:14 AM | 5:14 PM | 7:15 PM | 1:15 AM |
| 30 | 8:15 AM | meropenem + tazobactam (67 mg/kg of each) | 9:15 AM | 5:15 PM | 7:16 PM | 1:16 AM |
| 31 | 8:20 AM | piperacillin + tazobactam (67 mg/kg of each) | 9:20 AM | 5:20 PM | 7:21 PM | 1:21 AM |
| 32 | 8:21 AM | piperacillin + tazobactam (67 mg/kg of each) | 9:21 AM | 5:21 PM | 7:22 PM | 1:22 AM |
| 33 | 8:22 AM | piperacillin + tazobactam (67 mg/kg of each) | 9:22 AM | 5:22 PM | 7:23 PM | 1:23 AM |
| 34 | 8:23 AM | piperacillin + tazobactam (67 mg/kg of each) | 9:23 AM | 5:23 PM | 7:24 PM | 1:24 AM |
| 35 | 8:24 AM | piperacillin + tazobactam (67 mg/kg of each) | 9:24 AM | 5:24 PM | 7:25 PM | 1:25 AM |
| 36 | 8:25 AM | piperacillin + tazobactam (67 mg/kg of each) | 9:25 AM | 5:25 PM | 7:26 PM | 1:26 AM |
| 37 | 8:30 AM | drug 1 + 2 + 3 (67 mg/kg of each) | 9:30 AM | 5:30 PM | 7:31 PM | 1:31 AM |
| 38 | 8:31 AM | drug 1 + 2 + 3 (67 mg/kg of each) | 9:31 AM | 5:31 PM | 7:32 PM | 1:32 AM |
| 39 | 8:32 AM | drug 1 + 2 + 3 (67 mg/kg of each) | 9:32 AM | 5:32 PM | 7:33 PM | 1:33 AM |
| 40 | 8:33 AM | drug 1 + 2 + 3 (67 mg/kg of each) | 9:33 AM | 5:33 PM | 7:34 PM | 1:34 AM |
| 41 | 8:34 AM | drug 1 + 2 + 3 (67 mg/kg of each) | 9:34 AM | 5:34 PM | 7:35 PM | 1:35 AM |
| 42 | 8:35 AM | drug 1 + 2 + 3 (67 mg/kg of each) | 9:35 AM | 5:35 PM | 7:36 PM | 1:36 AM |
| 43 | 8:40 AM | positive control - linezolid (30 mg/kg) | 9:40 AM | 5:40 PM | 7:41 PM | 1:41 AM |
| 44 | 8:41 AM | positive control - linezolid (30 mg/kg) | 9:41 AM | 5:41 PM | 7:42 PM | 1:42 AM |
| 45 | 8:42 AM | positive control - linezolid (30 mg/kg) | 9:42 AM | 5:42 PM | 7:43 PM | 1:43 AM |
| 46 | 8:43 AM | positive control - linezolid (30 mg/kg) | 9:43 AM | 5:43 PM | 7:44 PM | 1:44 AM |
| 47 | 8:44 AM | positive control - linezolid (30 mg/kg) | 9:44 AM | 5:44 PM | 7:45 PM | 1:45 AM |
| 48 | 8:45 AM | positive control - linezolid (30 mg/kg) | 9:45 AM | 5:45 PM | 7:46 PM | 1:46 AM |
| 49 | 8:50 AM | vehicle (30% DMSO, 30% propylene glycol, 40% water) | 9:50 AM | 5:50 PM | 7:51 PM | 1:51 AM |
| 50 | 8:51 AM | vehicle (30% DMSO, 30% propylene glycol, 40% water) | 9:51 AM | 5:51 PM | 7:52 PM | 1:52 AM |
| 51 | 8:52 AM | vehicle (30% DMSO, 30% propylene glycol, 40% water) | 9:52 AM | 5:52 PM | 7:53 PM | 1:53 AM |
| 52 | 8:53 AM | vehicle (30% DMSO, 30% propylene glycol, 40% water) | 9:53 AM | 5:53 PM | 7:54 PM | 1:54 AM |
| 53 | 8:54 AM | vehicle (30% DMSO, 30% propylene glycol, 40% water) | 9:54 AM | 5:54 PM | 7:55 PM | 1:55 AM |
| 54 | 8:55 AM | vehicle (30% DMSO, 30% propylene glycol, 40% water) | 9:55 AM | 5:55 PM | 7:56 PM | 1:56 AM |

| ID | 4th dose SC | 5th dose SC | 6th dose SC | Bacterial detection results | Result |
|---|---|---|---|---|---|
| 1 | 8:30 AM | 4:30 PM | 12:31 AM | Plated: lawn of bacteria | Dead 4/6 |
| 2 | 8:31 AM | 4:31 PM | 12:32 AM | Plated: 11 colonies | Alive |
| 3 | 8:32 AM | 4:32 PM | 12:33 AM | Plated: 3 | Alive |

TABLE 7-continued

Data from Animal Experiments

| | | | | | | |
|---|---|---|---|---|---|---|
| 4 | 8:33 AM | 4:33 PM | 12:34 AM | colonies Liquid culture: no growth | Alive | |
| 5 | 8:34 AM | 4:34 PM | 12:35 AM | Liquid culture: growth | Dead | |
| 6 | 8:35 AM | 4:35 PM | 12:36 AM | Liquid culture: no growth | Alive | |
| 7 | 8:40 AM | 4:40 PM | 12:41 AM | Plated: lawn of bacteria | Dead | 0/6 |
| 8 | 8:41 AM | 4:41 PM | 12:42 AM | Liquid culture: growth | Dead | |
| 9 | 8:42 AM | 4:42 PM | 12:43 AM | Plated: 40 colonies | Dead | |
| 10 | 8:43 AM | 4:43 PM | 12:44 AM | Liquid culture: growth | Dead | |
| 11 | 8:44 AM | 4:44 PM | 12:45 AM | Liquid culture: no growth | Dead | |
| 12 | 8:45 AM | 4:45 PM | 12:46 AM | Plated: lawn of bacteria | Dead | |
| 13 | 8:50 AM | 4:50 PM | 12:51 AM | Plated: lawn of bacteria | Dead | 0/6 |
| 14 | 8:51 AM | 4:51 PM | 12:52 AM | Liquid culture: growth | Dead | |
| 15 | 8:52 AM | 4:52 PM | 12:53 AM | Plated: lawn of bacteria | Dead | |
| 16 | 8:53 AM | 4:53 PM | 12:54 AM | Liquid culture: growth | Dead | |
| 17 | 8:54 AM | 4:54 PM | 12:55 AM | Plated: lawn of bacteria | Dead | |
| 18 | 8:55 AM | 4:55 PM | 12:56 AM | Liquid culture: growth | Dead | |
| 19 | 9:00 AM | 5:00 PM | 1:01 AM | Plated: no colonies | Alive | 6/6 |
| 20 | 9:01 AM | 5:01 PM | 1:02 AM | Liquid culture: no growth | Alive | |
| 21 | 9:02 AM | 5:02 PM | 1:03 AM | Liquid culture: growth | Alive | |
| 22 | 9:03 AM | 5:03 PM | 1:04 AM | Plated: no colonies | Alive | |
| 23 | 9:04 AM | 5:04 PM | 1:05 AM | Plated: no colonies | Alive | |
| 24 | 9:05 AM | 5:05 PM | 1:06 AM | Liquid culture: no growth | Alive | |
| 25 | 9:10 AM | 5:10 PM | 1:11 AM | Liquid culture: growth | Alive | 5/6 |
| 26 | 9:11 AM | 5:11 PM | 1:12 AM | Plated: 1 colony | Dead | |
| 27 | 9:12 AM | 5:12 PM | 1:13 AM | Plated: no colonies | Alive | |
| 28 | 9:13 AM | 5:13 PM | 1:14 AM | Plated: 1 colony | Alive | |
| 29 | 9:14 AM | 5:14 PM | 1:15 AM | No blood obtained | Alive | |
| 30 | 9:15 AM | 5:15 PM | 1:16 AM | Liquid culture: growth | Alive | |
| 31 | 9:20 AM | 5:20 PM | 1:21 AM | Plated: 9 colonies | Dead | 4/6 |
| 32 | 9:21 AM | 5:21 PM | 1:22 AM | Plated: 1 colony | Alive | |
| 33 | 9:22 AM | 5:22 PM | 1:23 AM | Plated: 1 colony | Alive | |
| 34 | 9:23 AM | 5:23 PM | 1:24 AM | Liquid culture: no growth | Alive | |

TABLE 7-continued

Data from Animal Experiments

| | | | | | | |
|---|---|---|---|---|---|---|
| 35 | 9:24 AM | 5:24 PM | 1:25 AM | Liquid culture: no growth | Alive | |
| 36 | 9:25 AM | 5:25 PM | 1:26 AM | Liquid culture: growth | Dead | |
| 37 | 9:30 AM | 5:30 PM | 1:31 AM | Liquid culture: no growth | Alive | 6/6 |
| 38 | 9:31 AM | 5:31 PM | 1:32 AM | Liquid culture: no growth | Alive | |
| 39 | 9:32 AM | 5:32 PM | 1:33 AM | Plated: no colonies | Alive | |
| 40 | 9:33 AM | 5:33 PM | 1:34 AM | Plated: no colonies | Alive | |
| 41 | 9:34 AM | 5:34 PM | 1:35 AM | Liquid culture: no growth | Alive | |
| 42 | 9:35 AM | 5:35 PM | 1:36 AM | Plated: no colonies | Alive | |
| 43 | 9:40 AM | 5:40 PM | 1:41 AM | Liquid culture: no growth | Alive | 6/6 |
| 44 | 9:41 AM | 5:41 PM | 1:42 AM | Plated: no colonies | Alive | |
| 45 | 9:42 AM | 5:42 PM | 1:43 AM | Liquid culture: no growth | Alive | |
| 46 | 9:43 AM | 5:43 PM | 1:44 AM | Liquid culture: no growth | Alive | |
| 47 | 9:44 AM | 5:44 PM | 1:45 AM | Plated: no colonies | Alive | |
| 48 | 9:45 AM | 5:45 PM | 1:46 AM | Plated: no colonies | Alive | |
| 49 | 9:50 AM | 5:50 PM | 1:51 AM | Plated: lawn of bacteria | Dead | 0/6 |
| 50 | 9:51 AM | 5:51 PM | 1:52 AM | Liquid culture: growth | Dead | |
| 51 | 9:52 AM | 5:52 PM | 1:53 AM | Liquid culture: growth | Dead | |
| 52 | 9:53 AM | 5:53 PM | 1:54 AM | Liquid culture: growth | Dead | |
| 53 | 9:54 AM | 5:54 PM | 1:55 AM | Plated: lawn of bacteria | Dead | |
| 54 | 9:55 AM | 5:55 PM | 1:56 AM | Plated: lawn of bacteria | Dead | |

\* ~100 uL blood was plated for 3 samples to check for # of colonies
\* 100 uL of BHI was added to 3 tubes of blood and mixed and 100 uL of mixture was added to 4.9 mL BHI broth
1 colony from each plate with growth was added to BHI broth and grown o.n. and a glycerol stock prepared
A glycerol stock was prepared from each liquid culture showing growth

REFERENCES FOR THE EXAMPLES

1. Walsh, T. R., Weeks, J., Livermore, D. M. & Toleman, M. A. Dissemination of NDM-1 positive bacteria in the New Delhi environment and its implications for human health: an environmental point prevalence study. *The Lancet Infectious Diseases*, doi:10.1016/s1473-3099(11)70059-7 (2011).
2. Davies, J. Microbes have the last word. *EMBO Reports* 9, 302-317 (2007).
3. Davies, J. & Davies, D. Origins and Evolution of Antibiotic Resistance. *Microbiology and Molecular Biology Reviews* 74, 417-433, doi:10.1128/mmbr.00016-10 (2010).
4. Fuda, C. C. S., Fisher, J. F. & Mobashery, S. Beta-lactam resistance in *Staphylococcus aureus*: the adaptive resistance of a plastic genome. *Cellular and molecular life sciences: CMLS* 62, 2617-2633, doi:10.1007/s00018-005-5148-6 (2005).
5. Chambers, H. F. & Deleo, F. R. Waves of resistance: *Staphylococcus aureus* in the antibiotic era. *Nature reviews. Microbiology* 7, 629-641, doi:10.1038/nrmicro2200 (2009).
6. Malouin, F. & Bryan, L. E. MINIREVIEWS Modification of Penicillin-Binding of Beta-Lactam Resistance. *Antimicrobial agents and chemotherapy* 30, 1-5, doi:10.1128/AAC.30.1.1.Updated (1986).
7. Harrison, E. M. et al. A novel hybrid SCCmec-mecC region in *Staphylococcus sciuri*. *The Journal of antimicrobial chemotherapy*, 1-8, doi:10.1093/jac/dkt452 (2013).
8. Fuda, C., Suvorov, M., Vakulenko, S. B. & Mobashery, S. The basis for resistance to beta-lactam antibiotics by penicillin-binding protein 2a of methicillin-resistant *Staphylococcus aureus*. *The Journal of biological chemistry* 279, 40802-40806, doi:10.1074/jbc.M403589200 (2004).
9. Fuda, C. et al. Activation for Catalysis of Penicillin-Binding Protein 2a from Methicillin-Resistant *Staphylococcus aureus* by Bacterial Cell Wall. *J Am Chem Soc* 127, 2056-2057 (2005).
10. Otero, L. H., Rojas-Altuve, A., Llarrull, L. I., Carrasco-López, C. & Kumarasiri, M. How allosteric control of *Staphylococcus aureus* penicillin binding protein 2a enables methicillin resistance and physiological function. *Proceedings of the National Academy of Sciences of the United States of America* 110, 16808-16813, doi:10.1073/pnas.1300118110//DCSupplemental.www.pnas.org/cgi/doi/10.1073/pnas1300118110 (2013).
11. Villegas-Estrada, A., Lee, M., Hesek, D., Vakulenko, S. B. & Mobashery, S. Co-opting the Cell Wall in Fighting Methicillin-Resistant *Staphylococcus aureus*: Potent Inhibition of PBP 2a by Two Anti-MRSA β-Lactam Antibiotics. *J Am Chem Soc* 130, 9212-9213 (2008).
12. Long, S. W. et al. PBP2a mutations causing high-level Ceftaroline resistance in clinical methicillin-resistant *Staphylococcus aureus* isolates. *Antimicrobial agents and chemotherapy* 58, 6668-6674, doi:10.1128/AAC.03622-14 (2014).
13. Gu, B., Kelesidis, T., Tsiodras, S., Hindler, J. & Humphries, R. M. The emerging problem of linezolid-resistant *Staphylococcus*. *The Journal of antimicrobial chemotherapy*, doi:10.1093/jac/dks354 (2012).
14. van Hal, S. J., Paterson, D. L. & Gosbell, I. B. Emergence of daptomycin resistance following vancomycin-unresponsive *Staphylococcus aureus* bacteraemia in a daptomycin-naïve patient-a review of the literature. *European journal of clinical microbiology & infectious diseases: official publication of the European Society of Clinical Microbiology*, doi:10.1007/s10096-010-1128-3 (2010).
15. Arias, C. A. & Murray, B. E. Antibiotic-resistant bugs in the 21st century—a clinical super-challenge. *The New England journal of medicine* 360, 439-443, doi:10.1056/NEJMp0804651 (2009).
16. Bhusal, Y., Shiohira, C. M. & Yamane, N. Determination of in vitro synergy when three antimicrobial agents are combined against *Mycobacterium tuberculosis*. *International journal of antimicrobial agents* 26, 292-297, doi:10.1016/j.ijantimicag.2005.05.005 (2005).
17. Sjolund, M., Wreiber, K., Andersson, D. I., Blaser, M. & Engstrand, L. Long-Term Persistence of Resistant *Enterococcus* Species after Antibiotics To Eradicate *Helicobacter pylori*. *Ann Intern Med* 139, 483-488 (2013).
18. Tupin, A. et al. Resistance to rifampicin: at the crossroads between ecological, genomic and medical concerns. *International journal of antimicrobial agents* 35, 519-523, doi:10.1016/j.ijantimicag.2009.12.017 (2010).
19. Zhong, M. et al. An interesting case of rifampicin-dependent/-enhanced multidrug-resistant tuberculosis. *The international journal of tuberculosis and lung disease: the official journal of the International Union against Tuberculosis and Lung Disease* 14, 40-44 (2010).
20. Comas, I. et al. Whole-genome sequencing of rifampicin-resistant *Mycobacterium tuberculosis* strains identifies compensatory mutations in RNA polymerase genes. *Nature Genetics* 44, 106-110, doi:10.1038/ng.1038 (2011).
21. Fischbach, M. A. & Walsh, C. T. Antibiotics for emerging pathogens. *Science* (New York, N.Y.) 325, 1089-1093, doi:10.1126/science.1176667 (2009).
22. Zimmermann, G. R., Lehár, J. & Keith, C. T. Multi-target therapeutics: when the whole is greater than the sum of the parts. *Drug discovery today* 12, 34-42, doi:10.1016/j.drudis.2006.11.008 (2007).
23. Hegreness, M., Shoresh, N., Damian, D., Hartl, D. L. & Kishony, R. Accelerated evolution of resistance in multidrug environments. *Proceedings of the National Academy of Sciences of the United States of America* 105, 13977-13981, doi:10.1073/pnas.0805965105 (2008).
24. Lázár, V. et al. Bacterial evolution of antibiotic hypersensitivity. *Molecular Systems Biology* 9, doi:10.1038/msb.2013.57 (2013).
25. Imamovic, L. & Sommer, M. O. A. Use of Collateral Sensitivity Networks to Design Drug Cycling Protocols That Avoid Resistance Development. *Science Translational Medicine* 5, 204ra132-204ra132, doi:10.1126/scitranslmed.3006609 (2013).
26. Boucher, H. W. et al. Bad bugs, no drugs: no ESKAPE! An update from the Infectious Diseases Society of America. *Clinical infectious diseases: an official publication of the Infectious Diseases Society of America* 48, 1-12, doi: 10.1086/595011 (2009).
27. Rice, L. B. Antimicrobial resistance in gram-positive bacteria. *American journal of infection control* 34, S11-19; discussion S64-73, doi:10.1016/j.ajic.2006.05.220 (2006).
28. Alekshun, M. N. & Levy, S. B. Molecular mechanisms of antibacterial multidrug resistance. *Cell* 128, 1037-1050, doi: 10.1016/j.cell.2007.03.004 (2007).
29. Kumarasamy, K. K. et al. Emergence of a new antibiotic resistance mechanism in India, Pakistan, and the UK: a molecular, biological, and epidemiological study. *The Lancet Infectious Diseases* 3099, 1-6, doi: 10.1016/s1473-3099(10)70143-2 (2010).
30. Spratt, B. G. Properties of the penicillin-binding proteins of *Escherichia coli* K12. *European journal of biochemistry/FEBS* 72, 341-352 (1977).
31. Waxman, D. J. & Strominger, J. L. Penicillin-binding proteins and the mechanism of action of beta-lactam antibiotics. *Annual review of biochemistry* 52, 825-869, doi:10.1146/annurev.bi.52.070183.004141 (1983).
32. Lee, S. H. et al. Antagonism of chemical genetic interaction networks resensitize MRSA to β-lactam antibiotics. *Chemistry & biology* 18, 1379-1389, doi:10.1016/j.chembiol.2011.08.015 (2011).
33. Koga, T. et al. Affinity of Tomopenem (CS-023) for penicillin-binding proteins in *Staphylococcus aureus, Escherichia coli*, and *Pseudomonas aeruginosa*. *Antimicrobial agents and chemotherapy* 53, 1238-1241, doi:10.1128/aac.01433-08 (2009).
34. Yang, Y., Bhachech, N. & Bush, K. Biochemical comparison of imipenem, meropenem and biapenem: permeability, binding to penicillin-binding proteins, and stability to hydrolysis by beta-lactamases. *The Journal of antimicrobial chemotherapy* 35, 75-84 (1995).
35. Campbell, E. M. & Chao, L. A population model evaluating the consequences of the evolution of double-resistance and tradeoffs on the benefits of two-drug antibiotic treatments. *PloS one* 9, e86971-e86971, doi: 10.1371/journal.pone.0086971 (2014).
36. Munck, C., Gumpert, H. K., Wallin, A. I. N., Wang, H. H. & Sommer, M. O. A. Prediction of resistance development against drug combinations by collateral responses 37. Kuroda, M. et al. Whole genome sequencing of meticillin-resistant *Staphylococcus aureus*. *Lancet* 357, 1225-1240 (2001).
38. Goldstein, F. et al. Identification and phenotypic characterization of a β-lactam-dependent, methicillin-resistant *Staphylococcus aureus* strain. *Antimicrobial agents and chemotherapy* 51, 2514-2522, doi:10.1128/AAC.00040-07 (2007).
39. Arêde, P., Ministro, J. & Oliveira, D. C. Redefining the role of the β-lactamase locus in methicillin-resistant *Staphylococcus aureus*: β-lactamase regulators disrupt the MecI-mediated strong repression on mecA and optimize the phenotypic expression of resistance in strains with constitutive mecA. *Antimicrobial agents and chemotherapy* 57, 3037-3045, doi:10.1128/AAC.02621-12 (2013).
40. Berenbaum, M. C. What is Synergy? *Pharmacological Reviews* 1989 (1989).
41. Saiman, L. Clinical utility of synergy testing for multidrug-resistant *Pseudomonas aeruginosa* isolated from patients with cystic fibrosis: 'the motion for'. *Paediatric respiratory reviews* 8, 249-255, doi:10.1016/j.prrv.2007.04.006 (2007).
42. Clinical & Laboratory Standards, I. Performance Standards for Antimicrobial Susceptibility Testing; Nineteenth Informational Supplement. *CLSI* 29 (2009).
43. Clinical & Laboratory Standards, I. Methods for Dilution Antimicrobial Susceptibility Tests for Bacteria That Grow Aerobically; Approved Standard—Eighth Edition. *CLSI* 29 (2009).
44. AstraZeneca Pharmaceuticals, L. P. Merrem IV (meropenem) for injection for intravenous use only prescribing information. 1-7 (Wilmington, Del., 2013).
45. Fishovitz, J. et al. Disruption of Allosteric Response as an Unprecedented Mechanism of Resistance to Antibiotics. *Journal of the American Chemical Society* 136, 9814-9817 (2014).
46. Somani, P., Freimer, E. H., Gross, M. L. & Higgins, J. T. Pharmacokinetics of Imipenem-Cilastatin in Patients with Renal Insufficiency Undergoing Continuous Ambulatory Peritoneal Dialysis. *Antimicrobial agents and chemotherapy* 32, 4-9, doi:10.1128/AAC.32.4.530.Updated (1988).
47. Kinzig, M., Brismar, B. & Nord, C. E. Pharmacokinetics and Tissue Penetration of Tazobactam and Piperacillin in Patients Undergoing Colorectal Surgery. *Antimicrobial agents and chemotherapy* 36, 1997-2004, doi:10.1128/AAC.36.9.1997.Updated (1997).
48. Stutman, H. R., Welch, D. F., Scribner, R. K. & Marks, M. I. In vitro antimicrobial activity of aztreonam alone and in combination against bacterial isolates from pediatric patients. *Antimicrobial agents and chemotherapy* 25, 212-215 (1984).
49. Lee, S. H. et al. Antagonism of chemical genetic interaction networks resensitize MRSA to beta-lactam antibiotics. *Chem. Biol.* 18, 1379-1389, doi:10.1016/j.chembiol.2011.08.015 (2011).
50. Ankomah, P., Johnson, P. J. T. & Levin, B. R. The pharmaco-, population and evolutionary dynamics of multi-drug therapy: experiments with *S. aureus* and *E. coli* and computer simulations. *PLoS Pathogens* 9, e1003300-e1003300, doi:10.1371/journal.ppat.1003300 (2013).
51. Sonstein, S. A. & Baldwin, J. N. Loss of the penicillinase plasmid after treatment of *Staphylococcus aureus* with sodium dodecyl sulfate. *Journal of bacteriology* 109, 262-265 (1972).
52. Hackbarth, C. J. & Chambers, H. F. blaI and blaR1 regulate beta-lactamase and PBP 2a production in methicillin-resistant *Staphylococcus aureus*. *Antimicrobial agents and chemotherapy* 37, 1144-1149 (1993).
53. Lowy, F. D. Antimicrobial resistance: the example of *Staphylococcus aureus*. *Journal of Clinical Investigation* 111, 1265-1273, doi:10.1172/JCI200318535.In (2003).
54. Blazquez, B. et al. Regulation of the Expression of the β-Lactam Antibiotic-Resistance Determinants in Methicillin-Resistant *Staphylococcus aureus* (MRSA). *Biochemistry* 53, 1548-1550 (2014).
55. Craig, W. A. The pharmacology of meropenem, a new carbapenem antibiotic. *Clinical infectious diseases: an official publication of the Infectious Diseases Society of America* 24 Suppl 2, S266-275 (1997).
56. DeRyke, C. A., Banevicius, M. A., Fan, H. W. & Nicolau, D. P. Bactericidal activities of meropenem and ertapenem against extended-spectrum-β-lactamase-producing *Escherichia coli* and *Klebsiella pneumoniae* in a neutropenic mouse thigh model. *Antimicrobial Agents and Chemotherapy* 51, 1481-1486, doi:10.1128/AAC.00752-06 (2007).
57. Cai, Y., Wang, R., Pei, F. & Liang, B.-b. Antibacterial Activity of Allicin Alone and in Combination with Beta-Lactams against *Staphylococcus* spp. And *Pseudomonas aeruginosa*. *Journal of Antibiotics* 60, 335-338 (2007).
58. Berenbaum, M. C. A method for testing for synergy with any number of agents. *The Journal of infectious diseases* 137, 122-130 (1978).
59. Clinical & Laboratory Standards, I. Methods for Determining Bactericidal Activity of Antimicrobial Agents; Approved Guideline. *CLSI* 19 (1999).
60. Life_Technologies. SYBR® Select Master Mix for CFX User Guide. 1-34 (2012).
61. Li, H. et al. The Sequence Alignment/Map format and SAMtools. *Bioinformatics* 25, 2078-2079, doi:10.1093/bioinformatics/btp352 (2009).
62. Pfizer. Zosyn (Piperacillin and Tazobactam for Injection, USP) for injection for intravenous use only prescribing information. 1-26 (Philadelphia, Pa., 2012).
63. Merck. PRIMAXIN I.V. (IMIPENEM AND CILASTATIN FOR INJECTION). 1-17 (Whitehouse Station, N J, 2014).
64. Kumar, K. M., Anbarasu, A. & Ramaiah, S. Molecular docking and molecular dynamics studies on β-lactamases and penicillin binding proteins. *Mol. Biosyst.* 10, 891-900 (2014).
65. Petinaki et al. Detection of mecA, mecR1 and mecI genes among clinical isolates of methicillin-resistant staphylococci by combined polymerase chain reactions. *J. Antimicrob. Chemother.* 47, 297-304 (2001)
66. Nascimento et al. Potential spread of multidrug-resistant coagulase-negative staphylococci through healthcare waste. *J. Infect. Dev. Ctries.* 9, (2015)

What is claimed is:

1. A composition useful for the treatment of an infection caused by a methicillin-resistant *Staphylococcus aureus* (MRSA), wherein the resistance is due to a penicillin-binding protein 2a (PBP2a)-driven mechanism, the composition comprising:
   i) at least one carbapenem or another β-lactam capable of binding the allosteric site of PBP2a;
   ii) at least one β-lactamase inhibitor; and
   iii) at least one β-lactam that binds the open configuration of the active site of PBP2a;
wherein the composition is selected from the group consisting of
   a) meropenem/piperacillin/tazobactam (ME/PI/TZ);
   b) cefepime/piperacillin/tazobactam (CP/PI/TZ);
   c) aztreonam/piperacillin/tazobactam (AZ/PI/TZ);
   d) meropenem/amoxicillin/tazobactam (ME/AX/TZ);
   e) meropenem/amoxicillin/clavulanate (ME/AX/CV); and
   f) imipenem/piperacillin/clavulanate (IM/PI/CV).

2. The composition of claim 1, wherein the ratio of the carbapenem or another β-lactam to the β-lactamase inhibitor is in the range of 64:1 to 1:64.

3. The composition of claim 1, wherein the ratio of the carbapenem or another β-lactam to the PBP2a binding β-lactam is in the range of 64:1 to 1:64.

4. The composition of claim 1, wherein the ratio of the β-lactamase inhibitor to the PBP2a binding β-lactam is in the range of 64:1 to 1:64.

5. The composition of claim 1, wherein the ratio of the antibiotics in the combination may range from 64:1:1, 1:64:1, and 1:1:64 to 1:1:1.

6. A pharmaceutical composition comprising a composition of claim 1 and at least one pharmaceutically acceptable excipient.

7. A method for treating an infection caused by a methicillin-resistant *Staphylococcus aureus* (MRSA) in a subject, wherein the resistance is due to a penicillin-binding protein 2a (PBP2a)-driven mechanism, the method comprising administering to the subject an effective amount of a composition of claim 1.

8. A method for treating an infection caused by methicillin-resistant *Staphylococcus aureus* (MRSA), the method comprising administering to the subject an effective amount of a composition of claim 1.

* * * * *